(12) United States Patent
Endress et al.

(10) Patent No.: US 11,296,897 B2
(45) Date of Patent: Apr. 5, 2022

(54) COMPOSITE SECURITY MARKING AND METHODS AND APPARATUSES FOR PROVIDING AND READING SAME

(71) Applicant: Merck Patent GmbH, Darmstadt (DE)

(72) Inventors: Thomas Endress, Munich (DE); Daniel Szabo, Darmstadt (DE); Frederic Berkermann, Darmstadt (DE); Fabian Wahl, Buchs (CH)

(73) Assignee: MERCK PATENT GMBH, Darmstadt (DE)

( * ) Notice: Subject to any disclaimer, the term of this patent is extended or adjusted under 35 U.S.C. 154(b) by 623 days.

(21) Appl. No.: 16/023,884

(22) Filed: Jun. 29, 2018

(65) Prior Publication Data
US 2019/0334730 A1 Oct. 31, 2019

(30) Foreign Application Priority Data

Apr. 30, 2018 (EP) .................................... 18170044

(51) Int. Cl.
*H04L 9/32* (2006.01)
*G06K 9/00* (2006.01)
(Continued)

(52) U.S. Cl.
CPC ........ *H04L 9/3278* (2013.01); *G06K 19/0614* (2013.01); *H04L 9/3247* (2013.01); *H04L 67/1042* (2013.01)

(58) Field of Classification Search
CPC ........... G06K 19/0614; G06K 9/00577; G16H 40/20; H04L 67/1042; H04L 9/0866; H04L 9/3247; H04L 9/3278
See application file for complete search history.

(56) References Cited

U.S. PATENT DOCUMENTS

| 8,530,863 | B2 | 9/2013 | Lawandy |
| 8,534,544 | B1* | 9/2013 | Eker .................. G06K 19/10 |
| | | | 235/375 |

(Continued)

FOREIGN PATENT DOCUMENTS

| EP | 1927934 A2 | 6/2008 |
| EP | 2921989 A1 | 9/2015 |

(Continued)

OTHER PUBLICATIONS

PCT Search Report and Written Opinion issued in related application PCT/EP2019/060707, dated Aug. 12, 2019, 16 pages.

(Continued)

*Primary Examiner* — Theodore C Parsons
(74) *Attorney, Agent, or Firm* — Faegre Drinker Biddle & Reath LLP

(57) ABSTRACT

In one embodiment, the invention is directed to a method of reading a marking, comprising a stimulation step, wherein a physical challenge according to a predetermined challenge-response authentication scheme corresponding to the PUF is created and applied to a PUF; a detection step, wherein a response generated by the PUF in accordance with the challenge-response authentication scheme in reaction to the challenge is detected and a digital signal representing the response is generated; a processing step, wherein the digital signal is processed in order to generate a hash value of the response by application of a predetermined cryptographic hash function to the digital signal; and an output step, wherein data representing the generated hash value as a first reading result is output.

20 Claims, 14 Drawing Sheets

(51) Int. Cl.
*G06K 19/06* (2006.01)
*H04L 67/1042* (2022.01)

(56) References Cited

U.S. PATENT DOCUMENTS

| | | | |
|---|---|---|---|
| 10,320,569 B1 * | 6/2019 | Wentz | H04L 9/0866 |
| 2005/0131660 A1 | 6/2005 | Yadegar et al. | |
| 2011/0082824 A1 | 4/2011 | Allison et al. | |
| 2016/0048738 A1 | 2/2016 | He et al. | |
| 2018/0076957 A1 * | 3/2018 | Watanabe | G06Q 20/3829 |
| 2019/0052461 A1 * | 2/2019 | Kreder, III | H04L 9/3247 |

FOREIGN PATENT DOCUMENTS

| | | |
|---|---|---|
| EP | 2 999 156 A1 | 3/2016 |
| WO | 2005/032831 A1 | 4/2005 |
| WO | 2005/080088 A1 | 9/2005 |
| WO | 2007/031908 A2 | 3/2007 |
| WO | WO-2008080414 A1 | 7/2008 |

OTHER PUBLICATIONS

Carro-Temboury et al., "An optical authentication system based on imaging of excitation-selected lanthanide luminescence," Science Advances, vol. 4, No. 1, Jan. 26, 2018, 7 pages.

Fournier-Bidoz et al., "Facile and Rapid One-Step Mass Preparation of Quantum-Dot Barcodes," Angewandte Chemie International Edition, vol. 47, No. 30, Jul. 14, 2008, pp. 5577-5581.

Meruga et al., "Security printing of covert quick response codes using upconverting nanoparticle inks," Nanotechnology, IOP, Bristol, GB, vol. 23, No. 39, Sep. 11, 2012, pp. 1-9.

Extended European Search Report issued in related application EP 18170044.4, dated Oct. 26, 2018, 14 pages.

Popov, "The Tangle", IOTA Whitepaper for Jinn Labs, Version 1.3, Oct. 1, 2017, pp. 1-28.

* cited by examiner

US 11,296,897 B2

COMPOSITE SECURITY MARKING AND METHODS AND APPARATUSES FOR PROVIDING AND READING SAME

CROSS-REFERENCE TO RELATED APPLICATIONS

This application claims priority to European Application No. 18170044.4, filed Apr. 30, 2018, which is incorporated herein by reference in its entirety.

FIELD OF THE INVENTION

The present invention relates to the field of tracing and anti-counterfeit protection of products. Specifically, the invention is directed to a composite security marking comprising a physical unclonable function, PUF, to a physical object comprising such composite security marking and a method of providing same, and corresponding methods and reader devices for reading the marking. In particular, without limitation, such reader device can be used in connection with or can form a component of a multi-component security system, in particular of an anti-counterfeit protection and/or tracing system, which is also disclosed herein as part of an overall security solution for anti-counterfeit protection and secure product tracing.

BACKGROUND

In many industries, counterfeiting of products is a substantial problem that significantly impacts not only the revenues of original product manufacturers, but may even pose a serious threat to health and even life of consumers or operators of counterfeited, i.e. fake products. Such safety relevant product categories include in particular parts for automobiles and aircraft, components for the construction of buildings or other infrastructure, food, and even medical devices and pharmaceuticals.

Furthermore, in a broad range of different industries traceability of goods and physical objects is a key requirement. This applies in particular to logistics and supply chain infrastructures and to highly regulated/structured work flow environments. Examples are industry work places being controlled by official regulators such as the FDA (US Food & Drug Administration), and/or being certified e.g. according to GMP (Good manufacturing practice), GLP (Good laboratory practice), GCP (Good clinical practice), or DIN ISO or similar other standards and rules. Each of these regulated environments requires in particular an audit trail and auditable technologies. A further example is the traceability of high value products such as industrial spare parts in order to proof authenticity and intended use of these parts in secondary markets.

In order to limit counterfeiting and address in particular such safety concerns, and moreover to provide supply chain and work flow integrity, including recognition and authentication of products within work flows and supply chains, various industries have developed a number of different protection measures and identification solutions and identification solutions. Broadly used protection measures comprise adding a so-called security feature to a product, the feature being rather difficult to fake. For example, holograms, optically variable inks, security threads and embedded magnetic particles are known security features which are difficult to reproduce by counterfeiters. While some of these security features are "overt", i.e. can be easily seen or otherwise recognized by a user of the product, other security features are "covert", i.e. they are hidden and can only be detected by using specific devices, such as sources of UV-light, spectrometers, microscopes or magnetic field detectors, or even more sophisticated forensic equipment. Examples of covert security features are in particular printings with luminescent ink or ink that is only visible in the infrared part of the electromagnetic spectrum but not in its visible part, specific material compositions and magnetic pigments.

A specific group of security features, which are in particular used in cryptography, is known as "Physical Unclonable Functions" (PUFs). PUFs are sometimes also referred to as "Physically Unclonable Functions" or "Physical Random Functions". A PUF is a physical entity that is embodied in a physical structure and is easy to evaluate but hard to predict, even for an attacker with physical access to the PUF. PUFs depend on the uniqueness of their physical microstructure, which typically includes a random component that is already intrinsically present in the physical entity or is explicitly introduced into or generated in the physical entity during its manufacturing and which is substantially uncontrollable and unpredictable. Accordingly, even PUFs being produced by the exact same manufacturing process differ at least in their random component and thus can be distinguished. While in most cases, PUFs are covert features, this is not a limitation and overt PUFs are also possible. PUFs are furthermore ideal for enabling passive (i.e. without active broadcasting) identification of physical objects.

PUFs are known in particular in connection with their implementation in integrated electronic circuits by way of minimal unavoidable variations of the produced microstructures on a chip within given process-related tolerances, and specifically as being used for deriving cryptographic keys therefrom, e.g. in chips for smartcards or other security related chips. An example of an explanation and application of such chip-related PUFs is disclosed in the article "Background on Physical Unclonable Functions (PUFs)", Virginia Tech, Department of Electrical and Computer Engineering, 2011, which is available in the Internet at the hyperlink: http://rijndael.ece.vt.edu/puf/background.html.

However, also other types of PUFs are known, such as random distributions of fibers in paper used as a substrate for making banknotes, wherein the distribution and orientation of fibers can be detected by specific detectors and used as a security feature of the banknote. In order to evaluate a PUF, a so-called challenge-response authentication scheme is used. The "challenge" is a physical stimulus applied to the PUF and the "response" is its reaction to the stimulus. The response is dependent on the uncontrollable and unpredictable nature of the physical microstructure and thus can be used to authenticate the PUF, and thus also a physical object of which the PUF forms a part. A specific challenge and its corresponding response together form a so-called "challenge-response pair" (CRP).

Asymmetric cryptography, sometimes also referred to as "public key cryptography" or "public/private key cryptography" is a known technology based on a cryptographic system that uses pairs of keys, wherein each pair of keys comprises a public key and a private key. The public keys may be disseminated widely and are usually even publicly available, while the private keys are kept secret and are usually only known to their owner or holder. Asymmetric cryptography enables both (i) authentication, which is when the public key is used to verify that a holder of the paired private key originated a particular information, e.g. a message or stored data containing the information, by digitally signing it with his private key, and (ii) protection of information, e.g. a message or stored data, by way of encryption, whereby only the owner/holder of the paired private key can decrypt the message encrypted with the public key by someone else.

Recently, blockchain technology has been developed, wherein a blockchain is a public ledger in the form of a distributed database containing a plurality of data blocks and which maintains a continuously-growing list of data records and is hardened against tampering and revision by cryptographic means. A prominent application of blockchain technology is the virtual Bitcoin currency used for monetary transactions in the Internet. A further known blockchain platform is provided for example by the Ethereum project. In essence, a blockchain can be described as a decentralized protocol for logging transactions between parties, which transparently captures and stores any modifications to its distributed database and saves them "forever", i.e. as long as the blockchain exists. Storing information into a blockchain involves digitally signing the information to be stored in a block of the blockchain. Furthermore, maintaining the blockchain involves a process called "blockchain mining", wherein so-called "miners" being part of the blockchain infrastructure, verify and seal each block, such that the information contained therein is saved "forever" and the block can no longer be modified.

A further new ledger technology is known by the name of the "Tangle", which is blockless and permissionless distributed ledger architecture, which is scalable, lightweight, and provides a consensus in a decentralized peer-to-peer system. A prominent related technology using the Tangle as a technical basis is known as "IOTA", which is a transactional settlement and data integrity layer for the Internet of Things.

SUMMARY OF THE INVENTION

It is an object of the present invention to provide an improved way of effectively protecting a physical object against counterfeiting and tampering while allowing for efficiently recognizing and authenticating it in the course of an authorized examination thereof.

A solution to this problem is provided by the teaching of the appended independent claims. Various preferred embodiments of the present invention are provided by the teachings of the dependent claims.

Furthermore, a whole security solution is presented herein, including various apparatuses and methods as different aspects that may form part of an overall security solution for effectively tracing and protecting physical objects against counterfeiting and tampering.

A first aspect of the security solution provided herein is directed to a composite security marking for a physical object, in particular an anti-counterfeit composite security marking. The composite security marking comprises a physical unclonable function, PUF, and an encrypted representation of a digital signature and/or a representation of a pointer indicating a location where said digital signature can be accessed, wherein at least one of said representation of the pointer and said digital signature being accessible at the location is encrypted. The digital signature digitally signs a hash value resulting from application of a predetermined cryptographic hash function to data representing a response generated by the PUF in reaction to a challenge of a predetermined challenge-response authentication scheme.

The term "physical object", as used herein, refers to any kind of physical object, in particular to any kind of man-made or product or natural object, such as a vegetable or a piece of a natural raw material. Furthermore, as used herein, the term "physical object" may also refer to a person or an animal to which a composite security marking may be applied. A physical object may itself comprise multiple parts, e.g. a consumable good and a packaging thereof.

The term "composite security marking", as used herein, refers to a physical entity that comprises at least two different individual markings as its components, (hence "composite"), is adapted to be applied to or created on or in a physical object, and remains accessible after being applied to or created on or in the physical object in order to evaluate it. In the composite security marking according to the above first aspect of the security solution, a first component is a PUF and a second component is an encrypted representation of a digital signature or a representation of a pointer indicating a location where said digital signature can be accessed, wherein at least one of said representation of the pointer and said digital signature being accessible at the location is encrypted. In particular, the two or more components of the composite security marking may be located on or within a same substrate or part of the physical object. Alternatively, a subset of the components or all of them may be located on or within separate substrates or other parts of the physical object. The encryption may particularly be based on a known symmetric or an asymmetric encryption scheme, e.g. according to the well-known AES (symmetric) or RSA (asymmetric) cryptographic schemes.

The term "digital signature", as used herein, refers to a set of one or more digital values that confirms the identity of a sender or originator of digital data and the integrity of the later. To create a digital signature, a hash value is generated from the data to be protected by way of application of a suitable cryptographic hash function. This hash value is then encrypted with a private key (sometimes also called "secure key") of an asymmetric cryptographic system, e.g. based on the RSA cryptographic system, wherein the private key is typically known only to the sender/originator. Usually, the digital signature comprises the digital data itself as well as the hash value derived from it by the sender/originator. A recipient may then apply the same cryptographic hash function to the received digital data, use the public key corresponding to said private key to decrypt the hash value comprised in the digital signature, and compare the decrypted hash value from the digital signature to the hash value generated by applying the cryptographic hash function to the received digital data. If both hash values match, this indicates that the digital information has not been modified and thus its integrity has not been compromised. Furthermore, the authenticity of the sender/originator of the digital data is confirmed by way of the asymmetric cryptographic system, which ensures that the encryption using the public key only works, if the encrypted information was encrypted with the private key being mathematically paired to that public key. The representation of the digital signature may particularly be implemented using an RFID transmitter or a single- or multi-dimensional barcode, such as a QR-Code or a DATAMATRIX-code or simply as a multi-digit number.

The term "cryptographic hash function", as used herein, refers to a special type of hash function, i.e. a mathematical function or algorithm that maps data of arbitrary size to a bit string of a fixed size (a hash value), which is designed to also be a one-way function, i.e. a function that is easy to compute on every input, but hard to invert given the image of a random input. Preferably, the cryptographic hash function is a so-called collision resistant hash function, i.e. a hash function that is designed such that it is difficult to find two different data sets d1 and d2 such that hash(d1)=hash(d2). Prominent examples of such hash functions are the hash functions of the SHA-family, e.g. the SHA-3 function or the hash functions of the BLAKE family, e.g. the BLAKE2 function. In particular, so-called "provably secure cryptographic hash functions" may be used. These are hash functions for which a certain sufficient security level can be mathematically proven. In the present security solution, the security of the cryptographic hash function is further improved by the fact, that the reading of a marking comprising a PUF, particularly of a composite security marking, as disclosed herein, takes place at a particular location and time, where the physical object bearing the marking is actually present at such location and time. This can be used either to increase the absolute level of security that can be achieved or to allow for the use of cryptographic hash functions working with smaller data sets, e.g.

shorter data strings as inputs and/or outputs, while still providing a given required security level.

A "pointer indicating a location where said digital signature can be accessed", as used herein, may be in particular a pointer to a local or remote database or to a server address or Internet address, e.g. a hyperlink or similar, at which the digital signature can be accessed, e.g. downloaded. The pointer may particularly be implemented using an RFID transmitter or a single- or multi-dimensional barcode, such as a QR-Code or a DATAMATRIX-code as its representation The composite security marking according to the first aspect of the present security solution can be used by a first party, e.g. an originator of a physical object in the form of a product, to protect any physical object to which the components of the marking, i.e. at least a respective PUF and the corresponding digital signature of its response, can be applied. In particular, the marking is preferably applied to the physical object in such a way, that it cannot be separated again from the object without destroying the marking or at least parts thereof.

Already by nature, the PUF is "unclonable" and thus provides a first level of security, i.e. as a means of confirming the authenticity of the marking and thus of the physical object. This first security level is, however, further enhanced to a higher second security level by the combination of the PUF with the digital signature that cryptographically signs a hash value derived from a response by the PUF to a challenge of a predetermined challenge-response-scheme pertaining to the PUF. In this way, in analogy to a digital signature for electronic documents, a digital signature for physical objects is created for protecting such objects, particularly against counterfeiting. The encryption of the representation of a digital signature and/or the representation of the pointer indicating a location where said digital signature can be accessed adds yet another, i.e. third, level of security, because the respective representations first need to be decrypted, which requires knowledge of the encryption scheme and the correct cryptographic key, before the digital signature can be read.

In order to verify the authenticity of the physical object respectively its origin, a challenge according to this challenge-response-scheme is applied by a second party receiving the physical object to the PUF of the physical object's marking and the same cryptographic hash function is applied to generate a respective first hash value from data representing the response received from the PUF. The second hash value contained in the digital signature can be derived by decrypting the encrypted representation of the digital signature or the encrypted representation of the pointer, as applicable and decrypting the thus recovered digital signature using its related public key. Then the first and second hash values can be compared. If they match, this indicates that the physical object is authentic and the composite security marking has not been tampered with. Otherwise, i.e. if they do not match, this indicates that some sort of fraud might have happened since the originator applied the composite security marking to the physical object.

Accordingly, the composite security marking provides additional levels of security, and thus an improved way of protecting a physical object against counterfeiting and tampering. Furthermore, as the response of the PUF to a challenge according to the challenge-response-scheme yields digital data, e.g. a data string, the composite security marking can be used to protect any physical object to which such marking can be applied, even if the object itself does not provide any digital data.

In the following, preferred embodiments of the composite security marking are described, which can be arbitrarily combined with each other or with other aspects of the solution described herein, unless such combination is explicitly excluded, inconsistent or technically impossible.

According to a first preferred embodiment the PUF comprises an up-converting dye (UCD), preferably a plurality of different converting dyes. A UCD is a dye that shows the effect of photon up-conversion (UC), which is a process in which the sequential absorption of two or more photons leads to the emission of light at shorter wavelength than the excitation wavelength. It is an anti-Stokes-type emission. A typical example for such a process is the conversion of infrared light to fluorescent visible light. Materials by which up-conversion can take place often contain ions of d-block and f-block elements of the periodic system. Examples of these ions are $Ln3+$, $Ti2+$, $Ni2+$, $Mo3+$, $Re4+$, $Os4+$, and so on. Such materials typically comprise a relatively low portion of vibrionic spectral broadening and thus show fluorescence in very narrow bands of the electromagnetic spectrum. Using a variety of different combinations, i.e. mixes, of various up-converting substances, it is possible to generate huge number of distinguishable individual spectrums.

For example, assuming a spectral resolution of 20 nm within the spectral region of 400 nm to 800 nm, there are already $2^{20}$ different possibilities, if the detection is limited to the binary question of whether or not the spectrum shows a peak within the respective 20 nm interval. In other words, a binary value of "0" or "1" may be assigned to each interval, one of these values indicating presence of a peak in that interval and the other value indicating absence of such peak. Accordingly, a digital string can be formed from the 20 binary values assigned to the 20 intervals into which said spectral region is divided and thus $2^{20}$, i.e. approximately $10^6$ different combinations can be represented by such string. If instead an interval of only 10 nm is used, the numbers increased to $2^{46}$, i.e. approximately $10^{11}$ different combinations. If in addition, in each interval further distinction is made in case of each peak, e.g. whether the respective peak is closer to a "full" peak or to only a "half" peak (cf. FIG. 4(b)), then in the case of 40 intervals the number of combinations is even increased to $3^{40}$, i.e. approximately $10^{18}$ combinations. Accordingly, it is virtually impossible, to create a mix of UCDs in such a way, that it shows the same spectrum, as the original mix it seeks to clone.

In this way, UCDs can be used to create a PUF. An advantage of using UCDs for PUFs is that they can be applied to almost any physical object, e.g. as a component of a coating or a material from which the physical object or parts thereof are made. Furthermore, UCDs are typically covert features and cannot be easily recognized without sophisticated equipment. This can be used to further increase the achievable security level.

According to another preferred embodiment the PUF comprises an unclonable physical pattern or a structure configured to generate a virtual pattern in response to the challenge. In one variant of this embodiment, the pattern may comprise a huge number of microscopic particles the location and/or orientation of which represent an uncontrollable and unpredictable physical pattern that can be detected but not cloned by practical means. In another preferred variant, said structure configured to generate a virtual pattern comprises a microstructure being configured to create an optical speckle pattern when illuminated with light of a suitable light source. In particular, the microstructure may comprise a plurality of so-called quantum dots, i.e. very small semiconductor particles, which are only several nanometers in size, so that their optical and electronic properties differ from those of larger particles and which emit light of specific wavelengths if electricity or light is applied to them (i.e. as a challenge). The quantum dots' size, shape and material, which can be controlled during manufacturing, determine these wavelengths, and thus a huge variety of different emission spectrums can be created as responses of a related challenge-response-scheme. In another preferred variant, the microstructure may comprise a plurality of rod-shaped quantum materials (quantum rods), which offer a similar color conversion mechanism and extended color gamut as spherical quantum dots. The unique advantage of quantum rods is the emission of polarized light. Of course, also combinations of the above variants of microstructures are possible.

The term "light" as used herein, refers to electromagnetic radiation and may include, without limitation, radiation in the visible part of the electromagnetic spectrum. Light may for example also comprise ultraviolet or infrared radiation instead or in addition to visible radiation. A "speckle" pattern is an intensity pattern produced by the mutual interference of a set of many electromagnetic wavefronts of a same or similar wavelength, e.g. in the visible spectrum, but different phases and usually also different amplitudes. The intensity of the waves resulting from the interference varies randomly, at least in the spatial dimension. Typically, monochromatic and sufficiently coherent radiation, such as laser emission, is used for generating such speckle patterns.

In particular, the microstructure can be an integral microstructure such as a surface of a physical object showing a sufficient optical roughness, or it can comprise a plurality of separate parts, e.g. microscopic particles in a random distribution within a body (which is at least partially transparent to the radiation) or on a surface of a physical object.

Similar as for UCDs, an advantage of using such speckle-generating microstructures for PUFs is that they can be applied to almost any physical object, be it on its surface or even embedded within the object, if the latter is sufficiently transparent to the light needed to generate the speckle pattern. Because such microstructures typically have characteristic dimensions in the order of the wavelengths of the light, they may be made very small and are thus also typically covert features that cannot be easily recognized without sophisticated equipment. This again increases the achievable security level.

According to a further preferred embodiment, the PUF comprises at least one of the following: (i) an image in which hidden information is steganographically embedded; (ii) an image that is printed with an ink containing one or more types of upconverting dyes, UCD; (iii) a hologram containing hidden phase-coded or frequency-coded information. In particular, in addition to the above-mentioned covert security features, which increase the security level that can be achieved, the image respectively hologram may comprise or represent in addition an overt feature, e.g. a one-dimensional or multi-dimensional barcode, such as a QR-Code or DATAMATRIX-Code, in order to present further information. For example, such a code may overlay the image or hologram below that contains the covert feature or the image may be printed with ink containing a mix of UCDs. This allows for very space efficient implementations of PUFs comprising both covered security aspects and overt security features or other information, such as the digital signature of the composite security marking or product codes, manufacturer identities, production site information etc.

According to a further preferred embodiment, the representation of the digital signature and/or the pointer is implemented by one or more of the following: (i) an alphanumeric string; (ii) a graphical or image representation; (iii) a one-dimensional or multi-dimensional barcode; (iv) a device, e.g. a short-range wireless chip, such as an RFID chip, transmitting a signal carrying the representation of the digital signature or pointer. In particular, this embodiment may be combined with the immediately preceding embodiment. Furthermore, the digital signature and/or pointer may be represented by only a part of said string, graphical image representation, barcode or signal, respectively, each of which may in addition represent further information that may or may not be security related.

According to a further preferred embodiment, the composite security marking comprises said pointer and said pointer indicates a routing to a data source, such as a server in the internet, that is accessible through a data link, such as a connection to the internet or another network, and from which the digital signature is retrievable. In particular, this allows for a central management of the digital signatures of multiple physical objects in a server environment. Furthermore, this enables a centralized monitoring and control of the use of the managed digital signatures which can be used in many ways, for example for early detection of fraud attempts or supply chain optimization. Specifically, a trust center infrastructure may be used for such centralized monitoring and control. Optionally, the pointer may also contain or point to information regarding a product type, serial number or other information relating to the physical object being marked with a composite security marking.

According to a further preferred embodiment, wherein the PUF comprises a UCD, said data representing a response generated by the PUF in reaction to a challenge of a predetermined challenge-response authentication scheme for said UCD represents a spectral barcode having a continuous or a quantized range of allowed spectral values for a selected discrete subset of wavelengths, and/or a characteristic lifetime of a luminescence effect occurring in the response. This allows in particular for a determination and scaling of the number of bits or other information units that can be encoded by using the UCD of the PUF. If, for example, in each interval of the spectrum the corresponding spectral value is quantized into one of four spectral levels, that interval of the spectrum can be used to code two bits of information represented by the PUF. Adding also a quantization of the characteristic lifetime of the luminescence effect in that spectral interval, can be used to add further bits of information. A quantization can be preferable over a continuous range of allowed spectral values, as it may increase the robustness against distortions of the response generated by the PUF.

According to a further preferred embodiment, wherein the PUF comprises an unclonable physical pattern or a structure configured to generate a virtual pattern in response to the challenge, said data representing a response generated by the PUF in reaction to a challenge of a predetermined challenge-response authentication scheme for said unclonable physical pattern or structure configured to generate a virtual pattern represents at least one recognized aspect or portion of said physical pattern or said virtual pattern, respectively. In particular, said recognized aspect might relate to a statistical measure applied to the physical pattern or virtual pattern, such as an average distance between individual nodes of the pattern, a related variance or standard deviation, or any other statistical moment. Alternatively, according to another variant, said pattern may be scanned, e.g. in a matrix fashion, and thus converted into a string of bits, e.g. by using a discrimination threshold and representing matrix points showing a light intensity above the threshold by a "1" and all matrix points having a light intensity below the threshold as "0", or vice versa. In this way, patterns can be efficiently converted into data representing a response generated by the PUF in reaction to the corresponding challenge.

According to a further preferred embodiment, the composite security marking comprises at least one component resulting from an additive manufacturing process and the PUF is contained in or otherwise forms part of that component. In particular, the additive manufacturing process may be so-called 3D-printing process. Preferably, the PUF is provided already in the raw material, from which the component is made using the additive manufacturing process. In this way, the PUF can be introduced into the component without a need for modifications to the manufacturing data based on which the additive manufacturing process is performed. Furthermore, the extremely high flexibility and complexity provided by additive manufacturing methods, allows for a virtually endless variety of different PUFs and their arrangement on or within the physical object to be marked. This, again, can be used to further increase the security level that can be achieved with the composite security marking.

A second aspect of the solution provided herein is directed to a physical object, in particular a product, comprising a composite security marking according to the first aspect of the solution, preferably according to any one or more of its embodiments or variants described herein.

Specifically, according to preferred embodiments, the physical object is a product comprising one or more items for consumption or use and a packaging thereof, and the PUF of the composite security marking is arranged on or contained within at least one of the items for consumption or use, while the representation of or pointer to the digital signature is arranged on or within the packaging. Thus, in this embodiment, the composite security marking is formed on two different substrates. This might be advantageous especially in situations, where there is not enough space on the product itself to carry both the PUF and the digital signature. In one variant, the product is a pharmaceutical product comprising for example a bottle containing a liquid pharmaceutical or a blister pack containing tablets as an item for consumption and a cardboard box surrounding the bottle or blister pack as a packaging. The PUF of the composite security marking is a printed label placed on the bottle wherein the label is printed with an ink containing a secret mix of different UCDs. The digital signature corresponding to the PUF may be printed on the packaging in the form of a two-dimensional barcode, e.g. a QR-code or a DATAMATRIX code.

According to further preferred embodiments, the physical object comprises one or more of the following items for consumption (consumable goods) or use: a pharmaceutical or cosmetic compound or composition; a medical device; a laboratory equipment; a spare part or component of a device or system; a pesticide or herbicide; a seeding material; a coating, ink, paint, dye, pigments, varnish, impregnating substance, functional additive; a raw material for additive manufacturing of products. In particular, all of these items have in common that there is a need to prevent counterfeiting, in order to avoid malfunctions, health threats or other risks.

A third aspect of the solution provided herein is directed to a method of providing a physical object, in particular a product, with a composite security marking. The method comprises the following steps: (i) adding a physical unclonable function, PUF, to an object to be marked; (ii) applying a challenge of a predetermined challenge-response authentication scheme to at least one of said added PUFs to trigger a response according to said authentication scheme in reaction to said challenge; detecting said response; (iii) applying a predetermined cryptographic hash function to data representing said response to obtain a hash value; (iv) signing said hash value with a digital signature; and (v) adding an encrypted representation of the digital signature or a representation of a pointer indicating where the digital signature can be accessed, wherein at least one of said representation of the pointer and said digital signature being accessible at the location is encrypted, to the object to be marked.

Accordingly, a composite security marking is provided to the physical object, which comprises said PUF and, protected by encryption, its corresponding digital signature or a pointer thereto. Preferably, the PUF is a PUF as described above as a component of a composite security marking according to the first aspect of the present security solution, respectively its preferred embodiments and variants. The produced composite security marking produced by the method thus corresponds in particular to the composite security marking according to the first aspect of the present security solution. Preferably, the method further comprises generating a public/private key pair of an asymmetric cryptographic system and using the private key for creating said digital signature of said hash value and making said corresponding public key available, directly or indirectly, to a recipient of the object bearing the composite security marking.

Optionally, the composite security marking may comprise more than one PUF, particularly such as described above, and more than one digital signature derived from a PUF or a pointer thereto according to steps (ii) to (v), as described above. Accordingly, in a corresponding embodiment of a method, the additional digital signatures may be derived either by applying in step (ii) different challenges corresponding to different challenge-response-schemes to the same PUF, if supported by the latter, or by adding in step (i) two or more PUFs to the object to be marked and performing step (ii) for each of these PUFs. In both of these variants, steps (iii) through (v) follow for each of the responses, wherein for step (v) the pointer may point to the corresponding set of generated digital signatures. In this way, the achievable security level may be increased even further.

According to a further preferred related embodiment, the step of adding one or more PUFs to an object to be marked comprises one or more of the following: (a) adding one or more PUFs to a coating material to obtain a PUF-enhanced coating material and applying, e.g. by spraying, coating, infiltrating, printing or painting, the PUF-enhanced coating material to a physical object to be marked; (b) adding one or more PUFs, preferably by means of one or more chemical or mixing processes, to a raw material or an intermediate material, such as an ink or color, before or while producing thereof a physical object to be marked; (c) adding one or more PUFs to a raw material or fusion agent of an additive manufacturing process, e.g. 3D-printing process, for producing a physical object to be marked or at least a part of such object. In particular, the one or more PUFs may be added to the raw material or fusion agent before or during the additive manufacturing process. This allows an easy integration of the one or more PUFs into the object itself. Furthermore, the security level can be further increased, because as the one or more PUFs this become an integral component of the object, a removal, in particular a non-destructive removal, of the one or more PUFs from the object, can be effectively prevented.

A fourth aspect of the solution provided herein is directed to an apparatus for providing a physical object, in particular a product, with a composite security marking, wherein the apparatus is adapted to perform the method according to the third aspect of the solution, preferably according to any one or more of its embodiments or variants described herein. Accordingly, the description and advantages of the third aspect of the solution apply mutatis mutandis to the apparatus according to this fourth aspect.

A fifth aspect of the solution described herein is directed to a method of reading with a reader device a marking comprising a physical unclonable function, PUF, and a representation of a first digital signature and/or a representation of a pointer indicating a location where said first digital signature can be accessed. The marking may particularly be a composite security marking according to the first aspect, preferably according to any one or more of its embodiments described herein. The method comprises the following steps: (i) a stimulation step, wherein a physical challenge according to a predetermined challenge-response authentication scheme corresponding to the PUF is created and applied to a PUF; (ii) a detection step, wherein a response generated by the PUF in accordance with the challenge-response authentication scheme in reaction to the challenge is detected and a digital signal representing the response is generated; (iii) a processing step, wherein the digital signal is processed in order to generate a first hash value of the response by application of a predetermined cryptographic hash function to the digital signal; (iv) an acquisition step, comprising accessing said first digital signature to recover from it a second hash value signed therewith, by: (a) reading and decrypting the representation of the first digital signature in the marking based on a predetermined decryption scheme, or (b) reading the representation of the pointer in the marking and acquiring and verifying the first digital signature from the location indicated by the pointer, including decrypting the representation of the pointer or the first digital signature according to the decryption scheme, respectively; and (v) an output step, comprising outputting a first reading result comprising one or more of the following: (a) a representation of the first hash value and a representation of a second hash value recovered in the acquisition step, (b) a matching output indicating whether, according to at least one predetermined matching criterion, the first hash value matches said second hash value, (c) an output indicating a reading failure.

The term "stimulation", as used herein, refers to creating and applying to a PUF a physical challenge according to a predetermined challenge-response authentication scheme corresponding to the PUF. Specifically, a stimulation may comprise emitting electromagnetic radiation as a challenge that triggers a response according to the challenge-response authentication scheme, when it is applied to a PUF being sensitive to this particular radiation, e.g., if the PUF is a UCD at which an anti-Stokes effect generating the response can be triggered by said radiation. Accordingly, a "stimulator", as used herein, is a component of the reader device being adapted to create such stimulation and apply it to a PUF.

Detecting a response generated by a PUF, as used herein, refers to physically detecting a response generated by a PUF in reaction to a challenge in accordance with a corresponding challenge-response authentication scheme and generating a digital signal representing the response, e.g. by respective data being carried by the digital signal. Accordingly, the term "PUF-detector", as used herein, refers to a component of the reader device being adapted to perform the detection step. In particular, the PUF-detector may comprise a receiver for electromagnetic radiation being emitted by the PUF in response to the challenge applied to it by a stimulator.

The term "decryption scheme" as used herein refers to the combination of a specific decryption method, such as a decryption algorithm, and a corresponding cryptographic key to be used in connection with said decryption method in order to decrypt information being encrypted with a corresponding encryption method and key.

The term "verifying a digital signature" as used herein refers to the common approach of verifying the originality of a digital signature, particularly comprising reading it by applying the related public key of the assumed originator in order to examine whether it is original, i.e. signed with the related secret private key of said originator.

In order to apply the predetermined cryptographic hash function to the digital signal, the hash function may particularly act on the whole digital signal, e.g. a data representation of the complete digital signal, or only to a distinctive portion thereof, such as for example (i) a payload portion (or a distinctive subset thereof) of a digital signal being represented according to a communication protocol defining an overhead portion and a payload portion of the signal, or (ii) a portion of such signal falling into a specific time frame, e.g. into a defined time period following a start of the detection following application of the challenge to a PUF.

Accordingly, the method of reading according to this fifth aspect of the solution can be advantageously used to "read" markings comprising a corresponding PUF and provide the "reading" result as output data that can be used to verify whether or not the marking, or a physical object bearing the marking has been counterfeited or tampered with. In particular, the method may be used to "read" a composite security marking according to the first aspect of the solution, for example according to any one or more of its embodiments or variants described herein. Thus, the method of reading can form part of an overall solution that provides an additional level of security, and thus an improved way of protecting a physical object against counterfeiting and tampering. Furthermore, in case the digital signature as such is already represented in the marking, i.e. if no pointer is needed to access it from a remote location over a communication link, such as the internet or another network connection, this method does not even require any connection to such communication link and may thus be used in an "offline" mode, for example in locations in the field, where—at least temporarily—no communication link is available. If, however, such communication link is available, optionally also the "online" mode involving a representation of a pointer to the digital signature and accessing the digital signature from a location indicated by the pointer may be used instead or in addition to the former "offline" mode.

According to a preferred embodiment, the digital signal is generated in the processing step in such a way that it represents at least one PUF-specific distinctive property of the response that is, at least substantially, invariant under variations of the environmental conditions at which the response is detected. By way of example, such varying environmental conditions could be light conditions, temperature, air pressure or other parameters or properties of the environment to which the PUF is typically exposed during it being detected by the reader device. An advantage of this embodiment is an increased robustness of the method of reading and the reader device used therefore with respect to their capability of correctly reading markings comprising a corresponding PUF. This enables an even more reliable distinction between counterfeited or tampered markings and physical objects bearing such markings on the one hand, and markings/objects that have not been counterfeited or tampered with on the other hand.

According to a further preferred embodiment, detecting the response in the detection step comprises detecting at least one property of electromagnetic radiation emitted by the PUF as a response in reaction to the challenge and generating the digital signal such that it represents this response. This allows, in particular, for a contactless, wireless reading of a marking containing the PUF. Such a method of reading and a respective reading device can particularly be advantageously used to detect responses of PUFs that are very small or embedded under a surface of a marking/object or where the marking or the physical object bearing the marking is very sensitive to mechanical or chemical impacts that would typically go along with a contact-based reading method.

Specifically, according to a further and related embodiment, detecting the response in the detection step comprises detecting a characteristic lifetime of a luminescence effect occurring in the response as a property of electromagnetic radiation emitted by the PUF. Accordingly, the detection step may particularly comprise detecting the luminescent radiation at different subsequent points in time after a stimulation of a corresponding PUF in order to derive from the detected radiation a measure for a characteristic lifetime, such as a half-time or other measures of a decay time, for example. As such characteristic lifetimes of luminescence effects are mainly only material specific, they are invariant under a large variety of different environmental parameters and are therefore particularly suitable for characterizing the response of a corresponding PUF showing such an effect as a distinctive property.

According to a further related preferred embodiment detecting the response in the detection step comprises detecting a spectrum of the emitted radiation as a property of electromagnetic radiation emitted by the PUF. Furthermore, processing the digital signal in the processing step comprises determining from the digital signal one or more of the following: (i) the position (i.e. wavelength or frequency or a related parameter) of one or more characteristic features (e.g. peaks, gaps or minima within the spectrum); (ii) one or more statistical measures characterizing the spectrum (e.g. mean, median, variance, standard deviation or other statistical moments or measures); (iii) one or more quantized spectral values of the spectrum (e.g. of the detected intensities within an intensity spectrum of the radiation); (iv) a spectral barcode representing a continuous or a quantized range of allowed spectral values occurring in the spectrum, e.g. for a selected discrete subset of wavelengths. Also, each of these variants may provide an increased robustness of the method against varying environmental conditions at which the response is detected.

According to a further preferred embodiment, the output step comprises digitally signing data containing the generated first hash value and outputting the resulting digital signature as a part of the reading result. In this way, the method can be used particularly to initially generate a digital signature of a response generated by a PUF in reaction to a challenge of a predetermined challenge-response authentication scheme, e.g. during a manufacturing or commissioning process of products to be protected by a composite security marking, as disclosed herein. In particular, the generated digital signature can be incorporated in addition to the PUF into such composite security marking. Preferably, the method, e.g. the output step, further comprises generating a public/private key pair of an asymmetric cryptographic system and using the private key for creating said digital signature of said hash value and making said corresponding public key available, directly or indirectly, to a recipient of the object bearing the composite security marking.

A sixth aspect of the solution described herein is directed to a method of reading with a reader device a marking that comprises both an encrypted representation of a first digital signature and a representation of a pointer indicating a location where a second digital signature can be accessed. The marking may particularly be a composite security marking according to the first aspect, preferably according to any one or more of its embodiments described herein. The method comprises:

(i) an acquisition step comprising: (a) accessing the first digital signature, including a first hash value signed therewith, by reading and decrypting its representation in the marking based on a predetermined decryption scheme and by verifying it, and (b) accessing the second digital signature by reading the representation of the pointer and acquiring the second digital signature including a second hash value signed therewith from the location indicated by the pointer, including decrypting the representation of the pointer or the acquired digital signature based on said predetermined decryption scheme, respectively, and verifying the second digital signature;

(ii) an output step comprising outputting a first reading result comprising one or more of the following: (a) a representation of the first hash value and a representation of the second hash value, (b) a matching output indicating whether, according to at least one predetermined matching criterion, the first hash value matches the second hash value, (c) an output indicating a reading failure.

The method according to this sixth aspect of the solution provides a further way of verifying whether or not the marking, or a physical object bearing the marking has been counterfeited or tampered with. Unlike in the case of the method of the fifth aspect, the method of the sixth aspect does not require stimulating a PUF in the marking and reading a corresponding response of the PUF to the stimulation. Instead, the verification is based on the comparison of (i) a secured representation of the first hash value in the marking itself and (ii) a second hash value which is not present in the marking itself but can only be accessed remotely from a secure environment, e.g. a secured server in the internet or a blockchain. If the two hash values match, this is a strong indication that no tampering has occurred. In order to access the two hash keys knowledge of the decryption scheme is necessary. This method has the further advantage that the reader device does not have to have the capability to stimulate and read the response from a PUF. Accordingly, even a common personal computer or personal communication terminal, such as a smart phone, a tablet computer, a portable computer or even a desktop computer may serve as the reader device, if it has a sensor, such as a camera, to read the representations of the first digital signature and the pointer, a communication link, such as an internet or other network connection, to access the location indicated by the pointer, and one or more computer programs causing it to perform said method of the sixth aspect.

According to a preferred embodiment of any one or both of the methods of the fifth and sixth aspects, the output step of the respective method further comprises outputting at least a part—preferably the whole—of a reading result in the form of a one-dimensional or a multi-dimensional barcode. This enables the use of readily available barcode scanners for the further processing of the output provided by the output step, which may be particularly advantageous, where the reader device is integrated within or interacting with an automated production line or other processing line, where its outputs need to be further processed by algorithms processed by the line rather than by a human user.

According to a further preferred embodiment of any one or both of the methods of the fifth and sixth aspects, the respective method further comprises an authentication step, wherein a user is authenticated before permitting him or her to further operate the reader device in case of a successful authentication. This can be advantageously used to further increase the security of the solution by preventing unauthorized users from successfully interacting with the reader device and thus getting involved in the security chain provided by the present security solution. Furthermore, this can be used to acquire user identity or other user related information, which can be used to increase the transparency of the flow of physical objects being marked by the marking, particularly products, along a supply chain. In case of security concerns, this information can then be used to track down potential threats to the security provided by the overall solution and to identify locations or persons which might be related to such threats.

According to a further preferred embodiment of any one or both of the methods of the fifth and sixth aspects, the respective method further comprises a communication step, wherein at least a part of the reading result is communicated over a communication link to an opposing side. Particularly, the communication step might be adapted for sending and receiving data over a wireline, wireless, or optical communication link, such as by way of example and without limitation a communication link based on wireless LAN, Bluetooth, cellular network or a classical telephone line.

Such communication link may be used for a variety of different purposes, including for sending acquired information, e.g. the output provided in the output step, to an opposing side, which might for example be a central security instance, such as a trust center comprising a central security server, which might form a component of the present security solution.

Furthermore, according to a further related embodiment of any one or both of the methods of the fifth and sixth aspects, said respective communication step further comprises capturing and sending security-related information to a predetermined opposing side over the communication link. Said opposing side might for example be the trust center mentioned in the immediately preceding embodiment. In particular, such sending of security-related information may occur randomly, or may be specifically triggered according to a predetermined trigger scheme or remotely, e.g. by the opposing side. This allows for a remote monitoring of the security status of the reader device itself, and/or of security-related events the reader device is involved in. Such a security-related event might for example be a detection of a marking/object that has been counterfeited or tampered with, according to the output generated in the output step or other security-related information provided by the reader device.

Specifically, according to related preferred embodiments of any one or both of the methods of the fifth and sixth aspects, the respective security-related information comprises one or more of the following: (i) location information characterizing a current or past location of the reader device; (ii) user data characterizing or identifying a user of the reader device; (iii) network data characterizing the communication link; (iv) information characterizing an attempt or actual act detected by at least one sensor of the reader device or a corresponding reaction of the reader device (e.g. as described above); (v) authentication information generated by an authentication device provided in the reader device.

According to a further embodiment of any one or both of the methods of the fifth and sixth aspects, the respective method further comprises an information monitoring step, wherein a security event is detected in information contained in a signal received from the opposing side over the communication link. This step enables, in particular, a transition of the reader device into a safe mode or even its deactivation, in case an authorized opposing side, e.g. a central security center, sends information containing such security event to the reader device, in order to avoid any negative impact the reader device might otherwise have on the overall security system. Such negative impact might result, for example, if any compromising act such as an unauthorized intrusion or firmware/software modification at the reader device or a use by an unauthorized person or at an unauthorized location has occurred and been communicated to or otherwise detected by the opposing side.

According to a further preferred embodiment of any one or both of the methods of the fifth and sixth aspects, the respective method further comprises an access monitoring step, wherein one or more of the following are detected by means of one or more sensors as a security event: (i) an attempt or actual act of physical intrusion into the reader device, such as an opening of its housing; (ii) an attempt or actual act of locally or remotely accessing an internal control functionality of the reader device, e.g. its firmware, operating system or an application, wherein such access is not available to a user of the device in the course of its normal operation. Specifically, such attempted access might be directed to taking over control of the functionality of the reader device or to modifying same. Consequently, this embodiment may be advantageously used to further increase the security aspect of the present security solution, and particularly to protect both the reader device itself and the whole solution presented herein against unauthorized intrusion and tampering.

According to a further related preferred embodiment of any one or both of the methods of the fifth and sixth aspects, the respective method further comprises a security defense step, wherein one or more of the following security measures are performed in reaction to detection of a security event: (i) locking the reader device such as to limit or prevent its further use; (ii) self-destroying at least one functional part of the reader device or destroy data stored therein in order to prevent its further use or access by a user; (iii) output an error message. In particular, the security measures may be considered specific measures for turning the reader device into a safe mode or for deactivating it, as described above.

According to a further preferred embodiment of any one or both of the methods of the fifth and sixth aspects, the respective acquisition step further comprises acquiring from the marking a further digital signature or a pointer indicating a source where a particular further digital signature pertaining to the marking can be accessed. Furthermore, the output step further comprises outputting a representation of the acquired further digital signature as a second reading result. In particular, the composite security marking may be a marking as described herein in connection with the first aspect of the present security solution, e.g. according to preferred embodiments and variants thereof as described herein, where an object being marked by the marking is a product comprising one or more items of consumption or use and a packaging thereof. This embodiment enables the reader device to acquire, in addition to the response, further information comprised in the marking, which may particularly be supply chain information. On the one hand, this can be used for both (i) examining the marking/object in view of whether it has been counterfeited or tampered with, or not, and (ii) reading and outputting additional information, such as supply-chain or other logistics information. Furthermore, however, the combination of both uses (i) and (ii) can be utilized to further increase the security aspect of the present security solution, because such additional information, like supply chain information, can be used to retroactively identify locations or persons being involved in supply chain, where a potential fraud might have happened as well as potential related dates or time frames. Accordingly, a reader device adapted to perform the method of this embodiment is a dual-use or even multi-use device, which increases the ease of use and reduces the number of different devices needed to read the complete composite security marking.

According to related preferred embodiments of any one or both of the methods of the fifth and sixth aspects, the respective second reading result comprises one or more of the following information: (i) location information pertaining to a location where the second digital signature was acquired by the reader device; (ii) authentication information of a user of the reader device; (iii) time and/or date information indicating the point in time at which the second digital signature was acquired by the reader device; (iv) a product identification, serial number, and/or batch number of an object being marked by the marking; (v) an expiration date of an object being marked by the marking.

According to a further preferred embodiment of any one or both of the methods of the fifth and sixth aspects, the respective method further comprises a storage step, wherein the first reading result is stored into a block of a (first) blockchain or into one or more node of a blockless distributed ledger. This enables a secure, reliable storage of the reading results with very high data integrity, such that it is essentially impossible to manipulate or erase or otherwise taper with or lose such data, e.g. due to unintended or deliberate deletion or due to data corruption. Thus, the complete reading history remains available. Furthermore, the stored information can be accessed wherever access to the blockchain is available. This allows for a safe and distributed storage and access to the stored reading results, e.g. for integrity verification purposes such as checking whether a supplier of a product being marked with a composite security marking, as described herein, was in fact the originator of the product, or not. Based on this embodiment, the physical world, to which the marked objects and the markings themselves belong, can be connected to the power of blockchain technology. Thus, a high degree of traceability of the origin and supply chain of physical objects, such as products, can be achieved.

According to a further related preferred embodiment of any one or both of the methods of the fifth and sixth aspects: (i) the respective storage step further comprises storing the second reading result—at least in parts—into a block of second blockchain being separate from the first blockchain or into one or more nodes of a second blockless distributed ledger being separate from the first blockless distributed ledger, respectively; and (ii) storing the first reading result comprises storing data representing the first hash value into a block of the first blockchain or into one or more nodes of the first blockless distributed ledger, respectively. This allows for storing and thus saving both the first and second reading results, e.g. in the case of the method of the fifth aspect the one being derived from reading the PUF and the one being read from the second digital signature, into a respective blockchain or blockless distributed ledger, thus providing the advantages discussed in connection with the immediately preceding embodiment. Using different blockchains or blockless distributed ledgers for the two different reading results further provides the advantage of easily supporting a combination of an existing (second) supply chain for the second reading results with an additional first supply chain, for the first reading results. Accordingly, different access rights can be easily enabled and the management of the blockchains respectively blockless distributed ledgers can be in the hands of different authorities. In particular, this embodiment can be used to verify whether (i) a supplier of a product was in fact its originator, and (ii) whether the supply chain was as expected, or not.

According to a further related preferred embodiment of any one or both of the methods of the fifth and sixth aspects the respective storage step further comprises:

(a) If the storage step relates to blockchains:
   storing the data representing the first hash value into a block of the first blockchain further comprises storing a cross-blockchain pointer, which logically maps said block of the first blockchain to a corresponding block of the second blockchain, into said block of the first blockchain; and
   storing the data representing the second hash value in a block of the second blockchain further comprises storing a cross-blockchain pointer, which logically maps said block of the second blockchain to a corresponding block of the first blockchain, into the block of the second blockchain; and (b) if the storage step relates to blockless distributed ledgers:
   storing said at least one of said hash values into a node of the first blockless distributed ledger comprises storing a cross-ledger pointer, which logically maps the node of the first blockless distributed ledger to a corresponding node of the second blockless distributed ledger, into the node of the first blockless distributed ledger; and
   storing the supplementary information into a node of the second blockless distributed ledger comprises storing a cross-ledger pointer, which logically maps the node of the second blockless distributed ledger to a corresponding node of the first blockless distributed ledger, into the node of the second blockless distributed ledger.

In this way, the two blockchains or two blockless distributed ledgers, respectively, can be interconnected by the cross-blockchain pointers or cross-ledger pointers, respectively, which can be used to further increase the achievable security level of the present security solution. In particular, this can be used to track down attempts of tampering with or counterfeiting marked objects at different points along a supply chain. For example, this embodiment allows for tracking down a location and/or a point in time of such an attempt or, in case of a mandatory authentication at the reader device, an identification of a user being involved with such an attempt.

A seventh aspect of the present security solution is directed to a reader device for reading a marking, including particularly a composite security marking according to the first aspect of the present solution, wherein the reader device is adapted to perform the method of the fifth aspect or of the sixth aspect of the present security solution, or both, preferably, according to anyone or more of their respective embodiments and variants described herein. Therefore, what is described herein with respect to the fifth and sixths aspects, respectively, of the present security solution similarly applies to the reader device according to this seventh aspect.

Specifically, the reader device being adapted to perform the method of the fifth aspect may comprise as functional units (i) a stimulator being configured to perform the stimulation step; (ii) a PUF-detector being configured to perform the detection step; (iii) a processing device configured to perform the processing step; (iv) an acquisition device being configured to perform the acquisition step of this method; and (v) an output generator being configured to perform the output step of this method. The reader device being adapted to perform the method of the sixth aspect may comprise as functional units (i) an acquisition device being configured to perform the acquisition step of this method; and (ii) an output generator being configured to perform the output step of this method.

According to preferred embodiments, the reader device may further comprise one or more of the following: (vi) an authentication device configured to perform said authentication step; (vii) a communication device configured to perform said communication step; (viii) a monitoring device configured to perform said information monitoring step; (ix) a security device comprising at least one sensor and being configured to perform said access monitoring step; (x) a security defense arrangement being configured to perform said security defense step; (xi) a blockchain storing device configured to perform said storage step. Preferably, two or more of components (i) to (xi) may be combined or integrated into a multi-functional component of the reader device. For example, all components involving a processing of data, might be combined into or implemented as an integral multi-functional processing unit.

According to further preferred embodiments, the reader device is integrated or otherwise forms a component of one or more of the following: a handheld device, e.g. a product or barcode scanning device; a production, quality control or commissioning equipment; a production or quality control or commissioning line; a flying object, e.g. a drone; a robot, e.g. an agricultural robot; an agricultural machine. This allows for an integration of the reader device's functionality into a system having additional or broader functionality, particularly in an automated or semi-automated manner. For example, in the case of a production quality control or commissioning line the reader device may be integrated into the line in such a way that it automatically reads the markings, in particular composite security markings, on the products running along the line in order to perform an initial capturing of the related data. That captured data may then be stored into a related database or compared to already stored data for the sake of verifying that the production or commissioning line produces respectively commissions the intended set of products. Similarly, at one or more nodes of a supply chain, such as logistics centers, such reader devices may be integrated inline into identification and transport systems, e.g. conveyors, in order to automatically or semi-automatically (e.g. in the case of a handheld device) check and verify the authenticity of the products based on their markings, before shipping them to a next node in the supply chain. The same applies to a final node, i.e. to a recipient and/or end user of the products.

According to a further preferred embodiment, the reader device is a portable electronic communication terminal. Without limitation, the reader device may for example be a smart phone or portable computer, e.g. a tablet computer. This may particularly be applicable, if the reader device is adapted to perform the method of the sixth aspect of the present solution, i.e. when there is no need to read the PUF in the marking to be read. The communication link may then be established using the communication capabilities which are anyway present in the electronic communication terminal, e.g. for cellular communication. In some instances, such an electronic communication terminal may instead or in addition also be adapted to perform the method of the fifth aspect of the present solution. For example, a flash light of the terminal (e.g. smart phone or tablet) may serve as a stimulator being configured to perform the stimulation step, if the PUF is selected such that it can be stimulated with the flash light, e.g. if it contains a suitable UCD. Furthermore, a camera of the terminal may serve as a PUF-detector being configured to perform the detection step, if the signal the PUF emits in reaction to the stimulation (challenge) provided by the flash light is detectable with the camera. The camera may also serve as an authentication device configured to perform said authentication step in connection with a processor platform, which is typically anyway present in such terminals. The processor platform may also serve as a processing device configured to perform the processing step, and the output step, e.g. together with a display or a sound generator or another output means of the terminal. Furthermore, a communication section of the terminal may serve as a communication device configured to perform said communication step, etc.

An eighth aspect of the present security solution is directed to a computer program comprising instructions, which when executed on one or more processors of a reader device according to the seventh aspect cause the reader device to perform the method according to the fifth aspect or the sixth aspect, or both, of the present security solution. The computer program may particularly be loaded or otherwise stored in the communication terminal of the seventh aspect, thus adapting it to perform one or both of the methods of the fifth and sixth aspect of the present solution.

The computer program may be particularly implemented in the form of a data carrier on which one or more programs for performing the method are stored. This may be advantageous, if the computer program product is meant to be traded as an individual product in individual product independent from the processor platform on which the one or more programs are to be executed. In another implementation, the computer program product is provided as a file on a data processing unit, particularly on a server, and can be downloaded via a data connection, e.g. the Internet or a dedicated data connection, such as a proprietary or local area network.

BRIEF DESCRIPTION OF THE DRAWINGS

Further advantages, features and applications of the present security solution are provided in the following detailed description and the appended figures, wherein:

FIGS. 7A and 7C show a flow chart illustrating a second embodiment of a method of reading with a reader device a marking comprising a PUF, such as a composite security marking of FIG. 1, according to a preferred embodiment of the present security solution;

In the figures, identical reference signs are used for the same or mutually corresponding elements of the solution described herein.

DETAILED DESCRIPTION

A. Composite Security Marking

Figure 1:
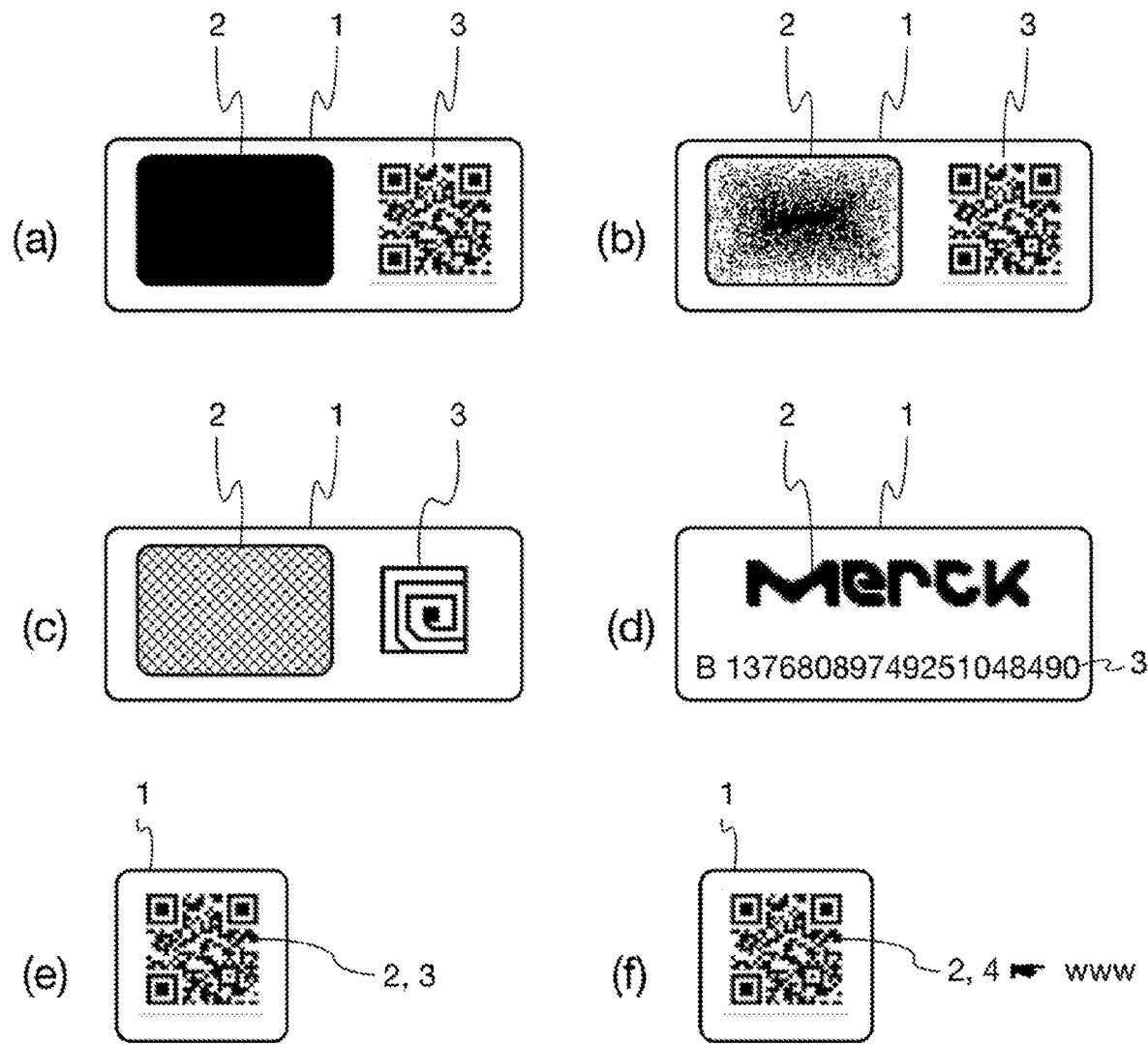
FIG. 1 schematically illustrates various composite security markings according to preferred embodiments of the present security solution.

FIG. 1 shows six different variations (a)-(f) of a composite security marking 1 for a physical object, esp. a product, according to preferred embodiments of the present security solution. Each of these composite security markings 1 comprises a PUF 2 and an encrypted representation of a digital signature 3 that digitally signs a hash value derived from data representing a response received from the PUF in reaction to a challenge corresponding to a predetermined challenge-response authentication scheme. Accordingly, the PUF 2 and the digital signature 3 are related and correspond to each other. The digital signature 3 was created with the help of a private key of a public key/private key pair of an asymmetric cryptographic system. After successfully decrypting it, it can be read, with the help of the corresponding public key of the asymmetric cryptographic system in order to verify the authenticity of the digital signature and thus the physical object marked with it. The encryption of the digital signature may be based on any suitable symmetric or asymmetric cryptographic system, e.g. AES or RSA.

Based on its nature, the PUF 2 can be considered unique (hence "unclonable") as is its response to the challenge. Accordingly, due to the collision resistant one-way nature of the cryptographic hash function also the hash value derived from the response is unique and thus pertains only to this exact PUF 2, as it is virtually impossible to have to identical hash values by applying said hash function to responses of different PUFs, and even more so, if the PUFs also have to be present at the same time at a same location (spatial and time coincidence).

Therefore, such a composite security marking 1 is extremely difficult, if not impossible, to fake and can thus be used to protect physical objects, such as products and other goods, in particular against counterfeiting and tampering.

FIG. 1(a) shows a first variant of such a composite security marking 1, wherein the PUF 2 is implemented as an area on the surface of the composite security marking 1 that contains a mix of UCDs already in its material or which has one or more additional layers containing a coating material or ink that contains such a mix of UCDs. The encrypted digital signature 3 is represented by a two-dimensional barcode, such as a QR code.

FIG. 1(b) shows another variant, wherein the PUF 2 is implemented as a microstructure in the form of a random distribution of a large number (e.g. $10^6$ or more) of light reflecting microscopic particles, which, when illuminated with coherent laser light of a specific wavelength as a challenge, create a characteristic speckle pattern by way of interference. The pattern can be detected with an optical sensor, such as a suitable digital camera, in order to generate data representing the response, e.g. as a digital image file.

FIG. 1(c) shows yet another variant, wherein the PUF 2 is implemented by a hologram that contains hidden phase-coded or frequency-coded information. When illuminated with coherent laser light of a specific wavelength as a challenge the hologram generates a virtual holographic image from which the hidden information can be extracted as a response according to a challenge-responsive authentication scheme with the help of one or more optical sensors and suitable image processing algorithms. In this variant, the digital signature 3 is exemplarily implemented by way of an RFID chip, which is configured to emit a signal representing the encrypted digital signature 3, when activated.

FIG. 1(d) shows yet another variant, wherein the PUF 2 is implemented by way of an image that is printed using ink containing a mix of different types of UCD's. Optionally, in addition hidden information may be steganographically embedded in the image. For example, there might be artificially created minimal specific color variations, which are invisible to the human eye, but which are used to encode such information and can be detected using suitable optical sensors in combination with respective analysis algorithms. In this variant, the encrypted digital signature 3 is exemplarily implemented as a numerical string.

FIG. 1(e) shows yet another variant, wherein both the PUF 2 and the encrypted digital signature 3 are implemented as an integrated combination, by way of a bar code image that is printed using ink containing a mix of different types of UCD's. The barcode encodes the encrypted digital signature 3, while the ink material represents the PUF 2. This allows for an extremely compact implementation of the composite security marking 1.

FIG. 1(f) shows yet another variant, wherein like in FIG. 1(e) both the PUF 2 and the encrypted digital signature 3 are implemented as an integrated combination, by way of a bar code image that is printed using ink containing a mix of different types of UCD's. However, in distinction to FIG. 1 (e), the barcode does not encode the encrypted digital signature 3 itself. Instead, it encodes a pointer 4 that indicates, where the actual digital signature 3 can be accessed from a place that is not part of the composite security marking 1 itself. Preferably, this pointer 4 is a representation of an Internet address, e.g. of a server, from where the digital signature 3 can be downloaded or otherwise accessed. Herein either the digital signature 3 or the pointer 4 or both are encrypted with said encryption system. Again, this allows for an extremely complex implementation of the composite security marking 1, and in addition allows a central management, storage and provision of the respective digital signatures 3 of multiple composite security markings 1, e.g. those pertaining to a particular series of products of a given manufacturer.

Figure 2:
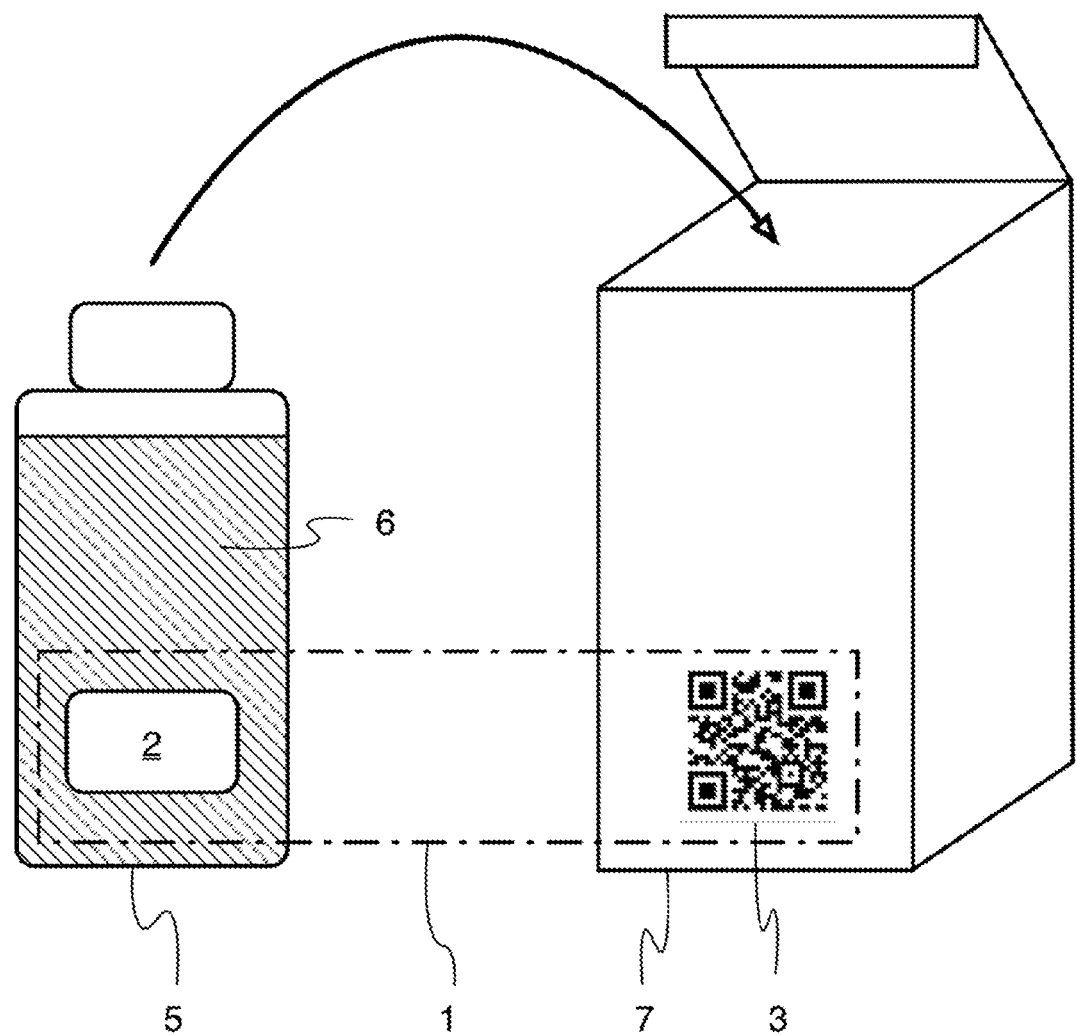
FIG. 2 schematically illustrates a multi-part physical object according to a preferred embodiment of the present security solution, the object comprising a bottled consumable good and a related packaging, wherein the object is marked with a composite security marking according to the present security solution that comprises a PUF implemented on the bottle and a corresponding digital signature printed on the packaging.

FIG. 2 shows a multi-part physical object according to a preferred embodiment of the present security solution. The object comprises a consumable good 6, such as a liquid pharmaceutical, that is contained in a container, esp. a bottle 5, and a related packaging 7. A composite security marking 1 is split into two parts on different substrates. As a first part of the composite security marking 1, a PUF 2 is placed on the bottle 5. The type of the PUF 2 can be any type of PUF as described herein, in particular as described in connection with FIG. 1 above. The second part of the composite security marking 1 comprises a barcode representing the encrypted digital signature 3 corresponding to the PUF 2 and being printed on the packaging 7. As the PUF 2 and the encrypted digital signature 3 are interlinked as described above, any counterfeiting by way of replacing the packaging 7 or the bottle 5 can be detected by way of identifying a mismatch between the hash value that can be derived from the response received in reaction to a related challenge according to the predetermined challenge-response authentication scheme and the hash value that is contained in and cryptographically protected by the encrypted digital signature 3.

Figure 3:
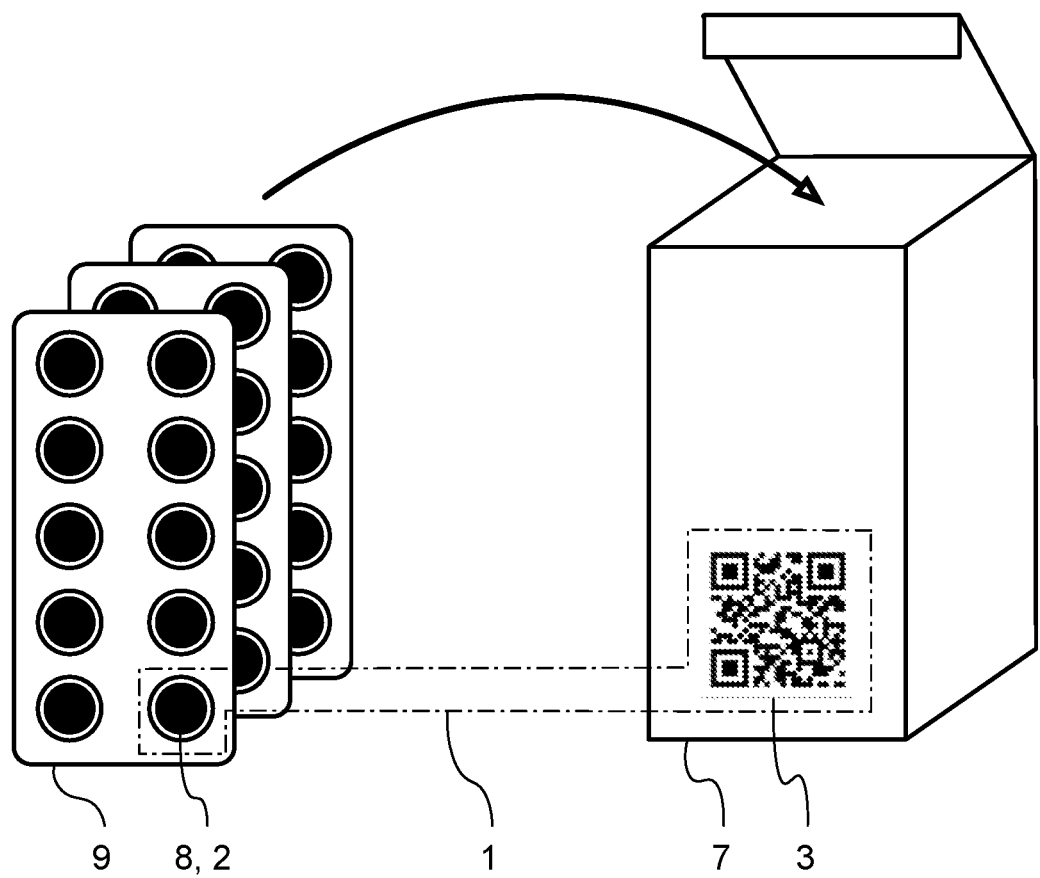
FIG. 3 schematically illustrates another multi-part physical object according to a preferred embodiment of the present security solution, the object comprising as consumable goods a set of pharmaceutical tablets arranged in blister packs and a related packaging for the blister packs, wherein each of the tablets contains a UCD-based PUF and the packaging comprises a printing thereon which represents a set of the digital signatures corresponding to the PUFs.

FIG. 3 shows another multi-part physical object according to a further preferred embodiment of the present security solution. Here, the products to be protected are pharmaceutical tablets (pills) 8 which are contained in a set of blister packs 9. Each of the tablets contains a mix of UCDs of a type which do not cause detrimental effects on a mammal, esp. a human body, when swallowed. The mix of UCDs may be the same for all tablets or, alternatively, even individual per tablet or a subset thereof. As in FIG. 2, a packaging 7 forms a second part of the physical object to be protected and bears the digital signature(s) 3 corresponding to the one or more PUFs 2 contained in the tablets 8. In this way, when the PUF 2 is an integral inseparable part of the consumable good itself, the level of security can be further enhanced in comparison to a situation according to FIG. 2, where only the container 5 for the consumable good is bearing the PUF 2.

Figure 4:
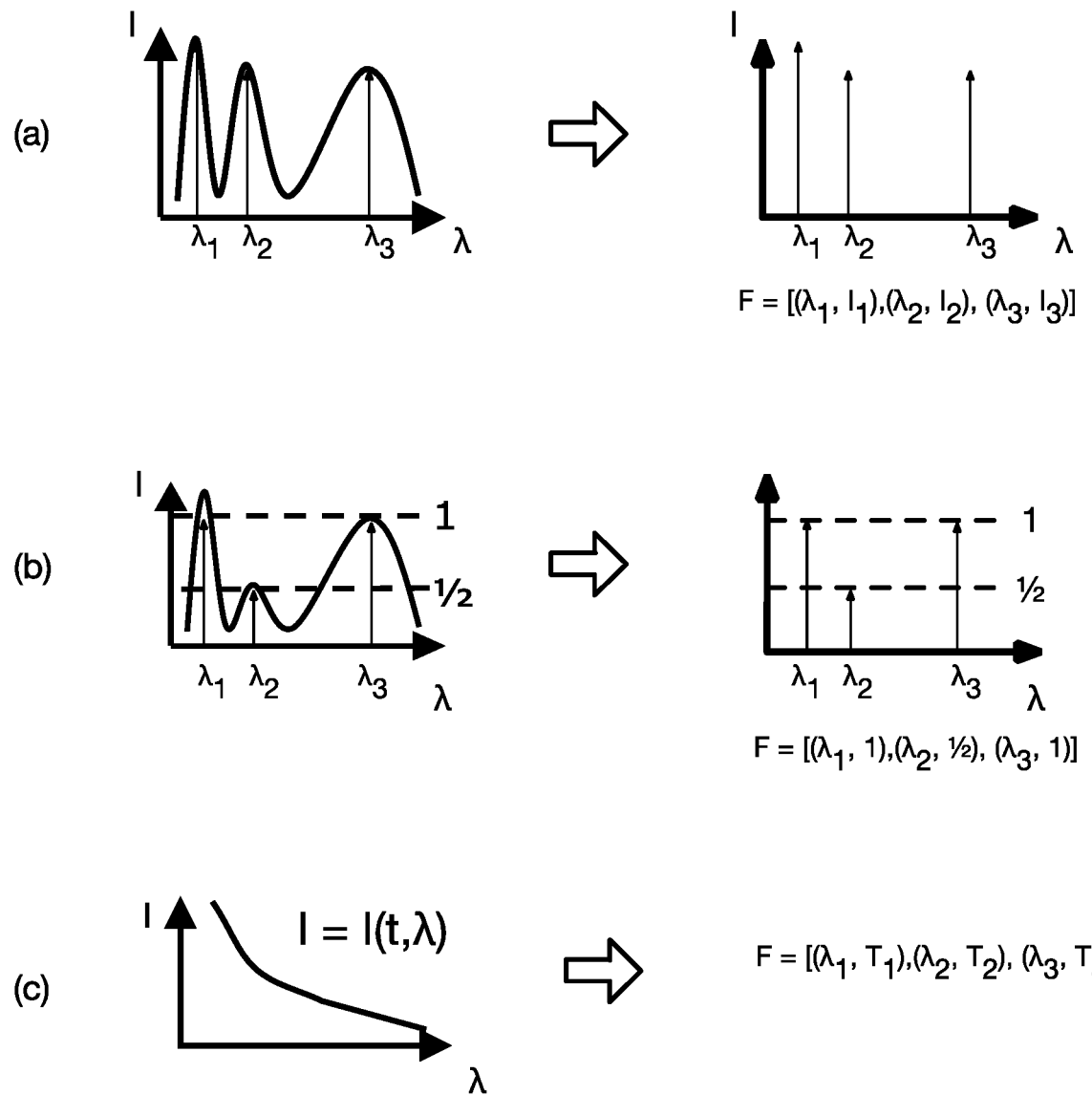
FIG. 4 illustrates various different ways of deriving data representing a response generated by a UCD-based PUF in reaction to a corresponding challenge of a predetermined challenge-response authentication scheme, according to preferred embodiments of the present security solution.

FIG. 4 illustrates various different ways (a)-(c) of deriving data representing a response generated by a UCD-based PUF 2 in reaction to a corresponding challenge of a predetermined challenge-response authentication scheme. In particular, the challenge may comprise irradiation of the PUF 2 by electromagnetic radiation having particular properties, e.g. a certain wavelength range or spectrum, such as particular spectral components in the infrared or UV part of the electromagnetic spectrum.

FIG. 4(a) shows a first variant, wherein a spectrum $I(\lambda)$ of an intensity I of light emitted by the PUF 2 in response to the challenge is detected as a function of the wavelength $\lambda$. In particular, selected wavelengths $\lambda_1, \lambda_2, \lambda_3, \ldots$, at which peaks of the spectrum $I(\lambda)$ occur, can be identified by way of spectrum analysis or even simply by use of adequate intensity thresholds. By way of example, and without limitation, this information can then be represented by a data string F, which in a simple form only represents the values of the respective wavelengths $\lambda_1, \lambda_2, \lambda_3$ etc. In an enhanced version, also the corresponding intensity values $I_1, I_2$ and $I_3$ etc. for these wavelengths are included in F, as indicated on the right side of FIG. 4(a). Alternatively, or in addition, other characteristics of the spectrum $I(\lambda)$ can be identified and represented by F. The data string F may in particular be a binary number consisting of a series of bits. Furthermore, the data string F can be interpreted as a "spectral barcode" which represents genuine features of the spectrum $I(\lambda)$, in particular in its graphical representation as shown on the right side of FIG. 4(a). In this variant, the intensity values I are analog values, i.e. they can have any value that can be represented by the data string F.

FIG. 4(b) shows another variant, which is similar to that of FIG. 4(a) with the exception that the intensity values I are quantized and can take on only one of three possible values, which in this example are normed values "0", "½" and "1" of a suitable intensity unit. This variant can be advantageously used to create a particularly robust way of representing the spectrum by the data string F, because due to the quantization the resulting data string F is less sensitive to variations in the detected values I caused by imperfections of the measurement itself. The data strings F of the variants shown in FIGS. 4(a) and 4(b) each form an implementation of a spectral barcode.

FIG. 4(c) shows yet another variant, wherein the intensity $I(t, \lambda)$ of luminescent light, preferably fluorescent light, emitted from a PUF as a response to the challenge is detected to as a function of the time t and wavelength $\lambda$. A characteristic lifetime $T=T(\lambda)$ is determined, which may for example correspond to the half-life period $T_{1/2}$ of the luminescent light of the wavelength $\lambda$. A corresponding data string F may again be formed as a representation of the response. In particular, the data string F may include the characteristic lifetimes $T_i(\lambda)$ and the related wavelengths $\lambda_i$, $i=1, 2, \ldots$ of a set of different wavelengths, which are preferably those wavelengths where peaks of the spectrum $I(\lambda)$ are detected.

While for the sake of simple illustration, the above examples have been described using a one-dimensional data string F as a representation of the response, other forms of data representations, in particular also multi-dimensional forms such as matrices, are also possible.

B. Providing a Physical Object With a Composite Security Marking

Figure 5:
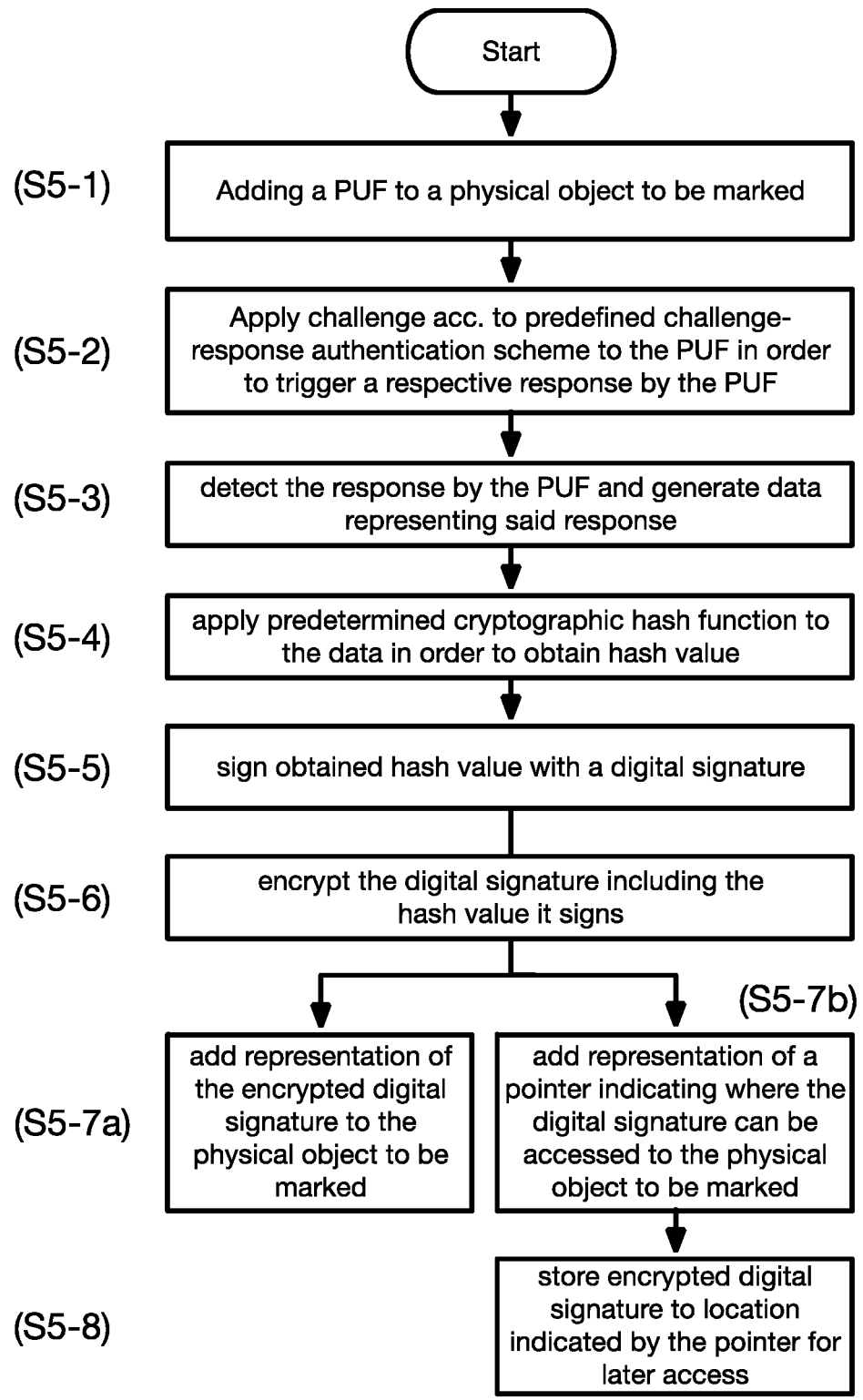
FIG. 5 show a flow chart illustrating a basic method of marking a physical object with a composite security marking, according to preferred embodiments of the present security solution.
Figure 6:
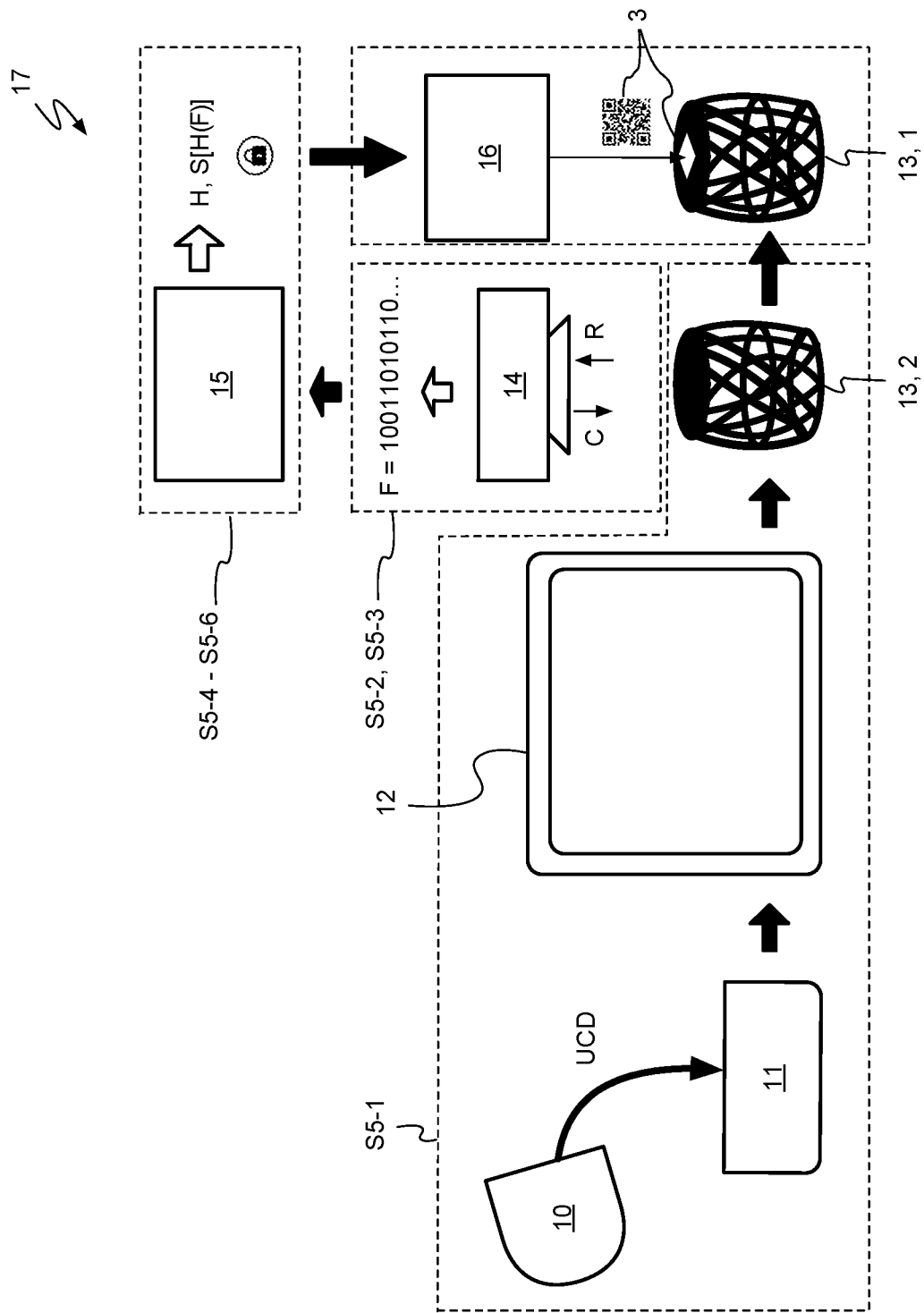
FIG. 6 schematically illustrates an apparatus for performing the method of FIG. 5, according to a preferred embodiment of the present security solution.

A method and an exemplary apparatus for providing a physical object with a composite security marking according to the present security solution, are illustrated in FIGS. 5 and 6.

Specifically, FIG. 5 is a flow chart illustrating a basic method of marking a physical object with a composite security marking. FIG. 6 schematically illustrates an apparatus 17 for performing the method of FIG. 5, according to a preferred embodiment involving an additive manufacturing process (3-D printing). The apparatus 17 comprises a 3-D printer 12, a PUF-scanner 14, a processing device 15 and a barcode printer 16. Furthermore, the apparatus 17 it may further comprise a container 11 for a raw material and means (not drawn) for mixing UCDs provided from a supply 10 with a 3D printing raw material. Optionally, some or all of these components 10 to 16 may be integrated into a same device.

In a first step S5-1 of the method, a PUF 2 (optionally a plurality of different PUFs) is added to a physical object to be marked, which may for example and without limitation be one of the pharmaceutical products illustrated in FIGS. 3 and 4, or a spare part, seeding material etc., as already discussed in the summary section above. In the case of the apparatus 17 of FIG. 6, the physical object will typically be a solid object that can be 3-D printed. In this case, step S5-1 may comprise adding one or more types of UCD (preferably a secret mix of UCDs) to the container 11 containing a raw material, e.g. in the form of a powder, suitable for 3-D printing. The UCD and the raw material are mixed, and then the resulting material mix is provided to the 3-D printer 12 as a 3-D printing material. With the help of the 3-D printer 12 a product 13, such as for example a medical device in the form of a mesh, is printed according to a product design specification delivered to the 3-D printer 12 by way of a respective design file. As the UCDs had been mixed into the raw material before printing, the resulting product 13 incorporates these UCDs, which together form one or more PUFs 2.

In a further step S5-2, the product 13 resulting from step S5-1 is exposed to a challenge C that is emitted by the PUF-scanner 14 in the form of electromagnetic radiation of a wavelength respectively wavelength range corresponding to the predetermined challenge-response authentication scheme pertaining to the PUF(s) 2 incorporated in the product 13. In a further step S5-3, which typically occurs substantially simultaneously with step S5-2, the PUF-scanner 14 detects a response R emitted by the PUF(s) 2 being incorporated in the product 13 in reaction to the challenge C. The response is then transformed into a data string F representing it, for example as described above in connection with FIG. 4. Particularly, and without limitation, the data string F may be a binary string, as illustrated. If there are two or more PUFs 2, the data string F may in particular represent the individual responses of all of these PUFs 2, which may optionally also be interpreted as a combined single response of a combined PUF comprising all of the individual PUFs.

In a further step S5-4, the data string F is provided to the processing device 15 as an input, which applies a predetermined cryptographic hash function H( . . . ) to the data string F, in order to generate a hash value H=H(F) representing the response R. In a further step S5-5, with the help of the processing device 15 the resulting hash value H is digitally signed with a private key of a public/private key pair of an asymmetric cryptographic system, such as the well-known RSA scheme, in order to generate a digital signature comprising the hash value H itself and a digitally signed version S[H(F)] thereof. Then, in a further step 5-6 the generated digital signature is encrypted with a suitable cryptographic scheme, e.g. RSA or AES, and a respective secret key thereof, to obtain the encrypted digital signature 3.

In a further step S5-7a, using the barcode printer 16, the encrypted digital signature 3 is printed to a surface of the product 13 in the form of a two-dimensional barcode, e.g. a QR-code or a DATAMATRIX code. As a consequence, the finished product 13 now comprises both the PUF(s) 2 and the corresponding encrypted digital signature (3) and thus a complete composite security marking 1 according to the present security solution.

In an alternative variant, a further step S5-7b is performed instead of step S5-7a. Step S5-7b is similar to step S5-7a, with the exception that instead of the encrypted digital signature 3 itself only a pointer 4 indicating where the encrypted digital signature 3 can be accessed, e.g. at a database or at an Internet server, is printed on the product 13. Before, simultaneously or after step S5-7b, a further step S5-8 is performed wherein the encrypted digital signature 3 obtained in step S5-6 is stored by the processing device over a data link to the location indicated by the pointer 4 for later access. According to a further related variant (not shown), step 5-6 comprises encrypting the pointer instead or in addition to the digital signature and step S5-7b consequently comprises adding a representation of a representation of the encrypted pointer to the physical object to marked. Accordingly, the pointer first needs to be decrypted, which requires knowledge of the respective decryption scheme and secret key, before it can be used to access the digital signature being stored at the location to which the pointer refers.

In both variants S5-7a and S5-7b, a representation of the encrypted digital signature 3 respectively of the (optionally encrypted) pointer 4 may be added, instead or in addition to printing, in the form of an electronic representation, e.g. a RFID chip that is arranged to emit a signal carrying said representation upon receiving a respective trigger signal (cf. FIG. 1(c)).

C. Reading of a Marking

The reading of a marking comprising a PUF, in particular of a composite security marking according to the first aspect of the present security solution, for example as shown and described in connection with FIG. 1, is now described in connection with corresponding FIGS. 7A to 9.

Figure 7A:
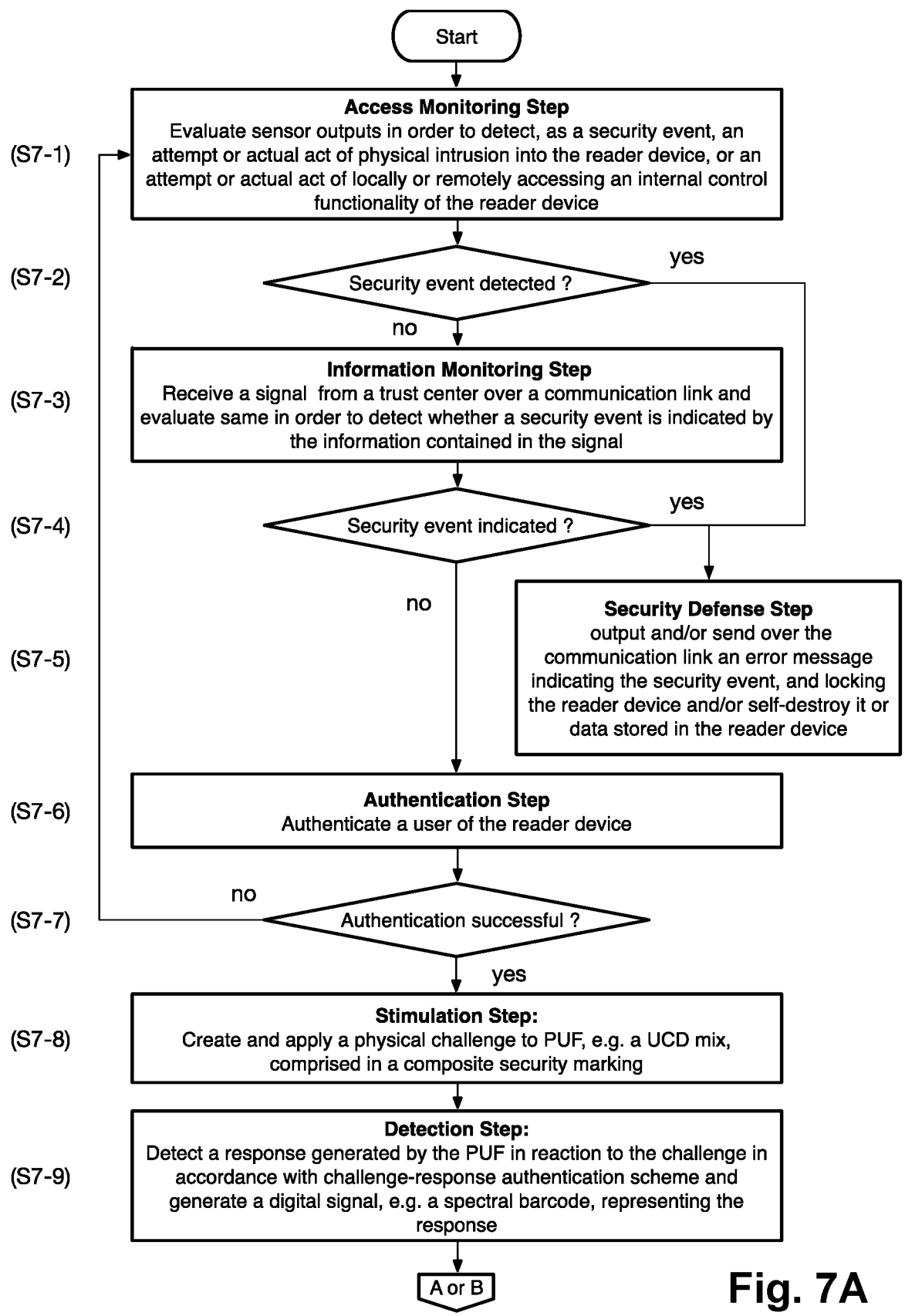
FIGS. 7A and B show a flow chart illustrating a first embodiment of a method of reading with a reader device a marking comprising a PUF, such as a composite security marking of FIG. 1, according to a preferred embodiment of the present security solution.
Figure 7B:
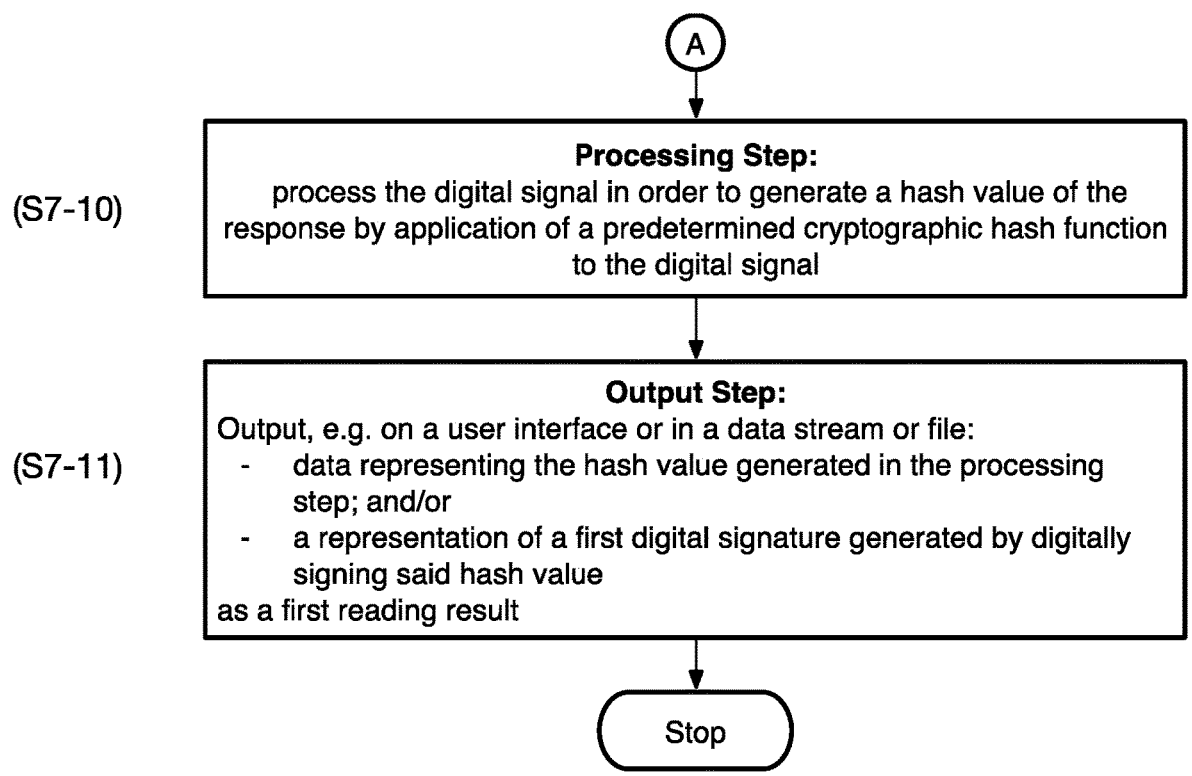

FIGS. 7A and 7B together show a flow chart (split in two parts connected via connector "A") illustrating an embodiment of a method of reading with a reader device a marking comprising a PUF, such as a composite security marking of FIG. 1. The method comprises, optionally, a first phase comprising steps S7-1 to S7-7, which serve for enhancing the security of a reader device itself that performs the method.

Step S7-1 is an access monitoring step, wherein sensor outputs are evaluated, in order to detect, as a security event, an attempt or actual act of physical intrusion into the reader device, or an attempt or actual act of locally or remotely accessing an internal control functionality, such as a processing device or communication device, of the reader device. If in a further step S7-2, it is determined that in step S7-1 a security event was detected (S7-2; yes), the method performs a security defense step S7-5, wherein an error message indicating the security event is output at a user interface and/or is sent over a communication link to an opposing side, such as a predetermined trust center. Furthermore, the reader device may be locked and/or the reader device or at least data stored therein may be self-destroyed in order to avoid unauthorized access to the data or any functionality of the reader device. Otherwise (S7-2; no), the method proceeds to an information monitoring step S7-3.

In the information monitoring step S7-3 a signal is received over a communication link from a central authority of the security solution, such as a trust center providing a security server, and is evaluated in order to detect whether a security event is indicated by the information contained in the signal. If in a further step S7-4, it is determined that in step S7-3 a security event was indicated in the information (S7-4; yes), the method proceeds to and performs the security defense step S7-5 as a final step.

Otherwise (S7-4; no), the method proceeds to an authentication step S7-5.

In the authentication step S7-5 a user of the reader device is authenticated, e.g. via a suitable user interface, such as a keyboard for inputting a password or a fingerprint sensor etc. If in a further step S7-7, it is determined that the authentication of step S7-6 failed (S7-7; no), the method returns to step S7-1 or, alternatively, to the authentication step S7-6 (not drawn). Otherwise (S7-7; yes), the method proceeds to a second phase, wherein the marking is read, and a reading result is output.

This second phase comprises a stimulation step S7-8, wherein a physical challenge according to a predetermined challenge-response-scheme corresponding to a PUF comprised in the marking is created and applied to the PUF, which might contain for example a mix of different UCDs.

Subsequently or simultaneously with the stimulation step S7-8, a detection step S7-9 is performed, wherein a response generated by the PUF in reaction to the physical challenge and according to the challenge-response authentication scheme is detected and a digital signal is generated that represents the response and which might for example take the form of or include a spectral barcode, as discussed above.

In a subsequent processing step S7-10 the digital signal is processed in order to generate a hash value of the response by application of a predetermined cryptographic hash function to the digital signal. Optionally, the processing step may further comprise digitally signing said hash value in order to provide a (first) digital signature thereof.

The processing step S7-10 is followed by an output step S7-14, wherein a (first) reading result is output, for example on a user interface of the reader device or in a data stream or file provided at an electronic or optical interface of the reader device. The (first) reading result comprises data representing the hash value generated in the processing step and/or a representation of said (first) digital signature. Accordingly, this method can be used to read a marking comprising a PUF, in particular a composite security marking, as disclosed herein (e.g. in FIG. 1) and to output a corresponding reading result that is based on the response generated by the PUF. The method of FIGS. 7A and 7B is particularly useful for initially reading a PUF at a manufacturing site or logistics site to obtain the (first) hash value and/or a digital signature thereof, before a product being marked with the respective composite security marking is sent into a supply chain.

Figure 7C:
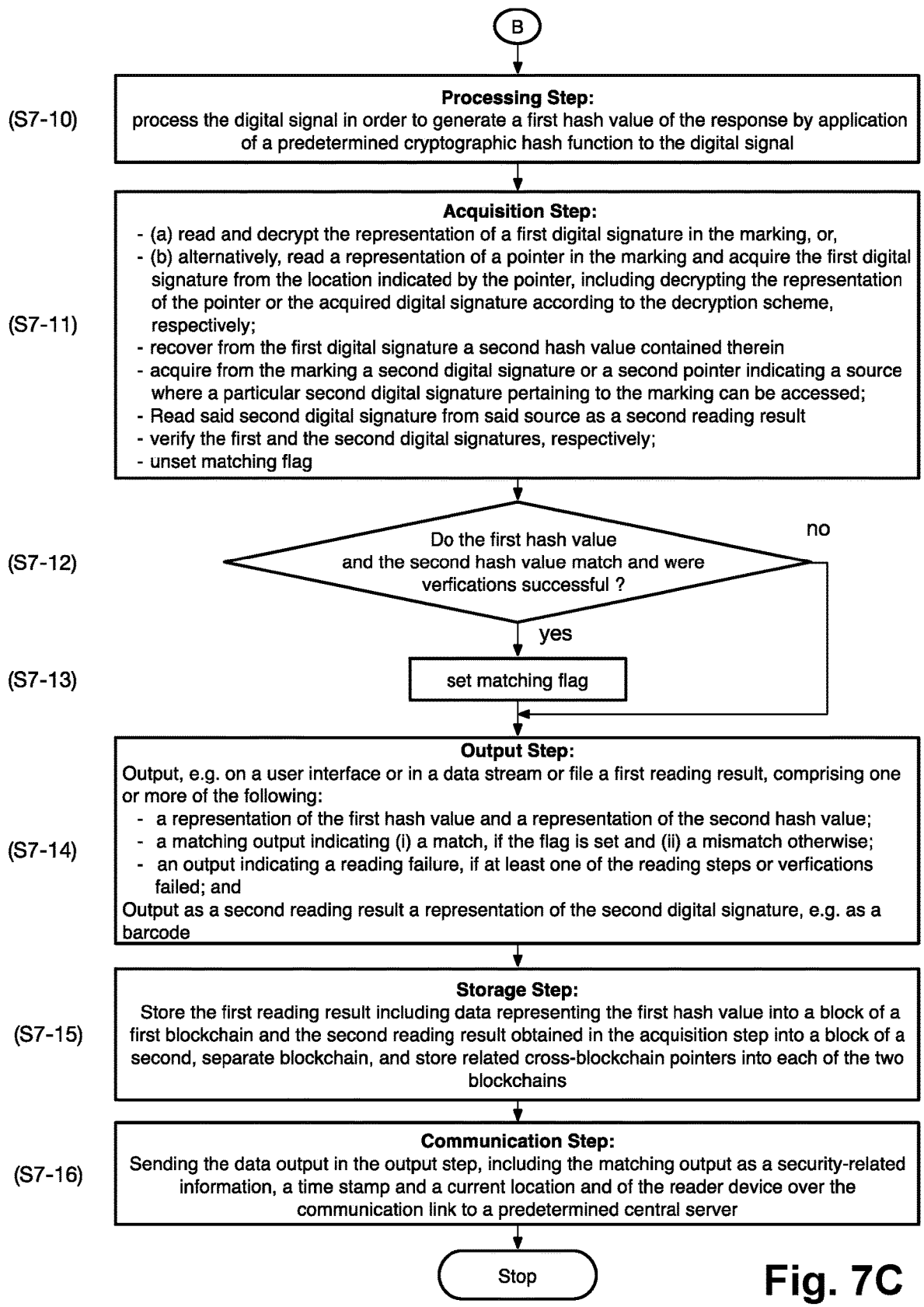

FIG. 7C (in connection with FIG. 7A) illustrates an embodiment of another method of reading a marking, which is particularly suitable for being used "in the field", i.e. at one or more nodes of a supply chain for the product, comprises the same steps S1 to S9 as the method of FIGS. 7A and 7B and accordingly the first part of the method is again illustrated in FIG. 7A. The method further comprises a similar processing step S7-10 as the method of FIG. 7B and an additional acquisition step S7-11, comprising accessing said first digital signature to recover from it a second hash value contained therein. This is achieved by either reading and decrypting the representation of the first digital signature in the marking, if any, based on a predetermined decryption scheme, and/or by reading a representation of a respective pointer in the marking and acquiring the first digital signature from the location indicated by the pointer, including decrypting the representation of the pointer or the acquired digital signature (i.e. information assumed to be such digital signature) according to the decryption scheme, respectively, i.e. depending on which is encrypted. In addition, in the embodiment of FIGS. 7A and 7C, the acquisition step further comprises acquiring from the marking a second digital signature or a pointer indicating a source where such second digital signature can be accessed, e.g. from a remote server.

The second digital signature is read from the marking or the said source, respectively, as a second reading result. Also, a matching flag is initialized (unset). Both, the first and the second acquired digital signatures are verified to confirm the originality, or otherwise, detect a counterfeiting or other unauthorized manipulation. The acquisition step S7-11 may be performed before, simultaneously, or after the processing step S7-10.

In a subsequent matching step S7-12, the first and second hash values are compared according to a predetermined comparison scheme, which may particularly be a simple equality test of all corresponding digits of the two hash values, although other comparison schemes are also possible. If the two hash values match (S7-12; yes) and the verifications were successful, the matching flag is set (step S7-13), otherwise (S7-12; no) the matching flag is not set. Of course, using such a matching flag is only one of many different possible implementations of determining and communicating whether or not the two hash values match.

The method further comprises an output step S7-14, wherein the first and the second reading results are output, for example on a user interface of the reader device or in a data stream or file provided at an interface such as an electronical or an optical interface of the reader device. In particular, the first reading result comprises one or more of the following: (a) a representation of the first hash value and a representation of the second hash value (b) a matching output indicating (i) a match, if the flag is set and (ii) a mismatch otherwise; (c) an output indicating a reading failure, if at least one of the reading steps or verifications of the digital signatures failed. The second reading result comprises a representation of the read (further) digital signature, i.e. of all or a part of the information signed therewith, e.g. as a barcode. Accordingly, also this method can be used to read a marking comprising a PUF, particularly a composite security marking, as disclosed herein (e.g. in FIG. 1) and to output a corresponding (first) reading result that is based on the response generated by the PUF.

The output reading results may be used for authentication purposes in the field (e.g. at various nodes along a supply chain of products being marked), or even initially at a fabrication or commissioning site, when a physical object is initially marked, in order to verify the marking and in order to capture its response for further use, e.g.

for storing it in a database for subsequent authentication purposes. The second reading result may be used particularly for tracking and tracing the flow of marked products at the point along a supply chain, where the marking is read by a reader device based on the method of FIGS. 7A and 7C.

The method further comprises a storage step S7-15, which is preferably performed simultaneously or after the output step S7-14. In the storage step S7-15 the first reading result comprising data representing the first hash value is stored into a block of a first blockchain and the second reading result obtained in the acquisition step S7-11 is stored into a block of a second, separate blockchain. Furthermore, related cross-blockchain pointers connecting the two blockchains are stored into each of the two blockchains to indicate the blocks in each of the blockchains, which correspond to each other in this sense, that they contain data created and stored at the same reading event. In particular, the second blockchain might be related to supply-chain information, such as time, location and user identification of the current reading event. The first blockchain, on the other hand, is used for tracking the authentication information, in particular, whether or not at the current reading event the physical object bearing the marking has been successfully authenticated as being original (i.e. not counterfeited or tampered with).

Furthermore, the method may comprise a communication step S7-16, wherein the data output in the output step, including the matching output, and optionally also a time-stamp and/or a current location of the reading event respectively the reader device (each of which can be considered security-related information) is sent over a communication link to a predetermined central server, which may for example form a part of a trust center.

Figure 8A:
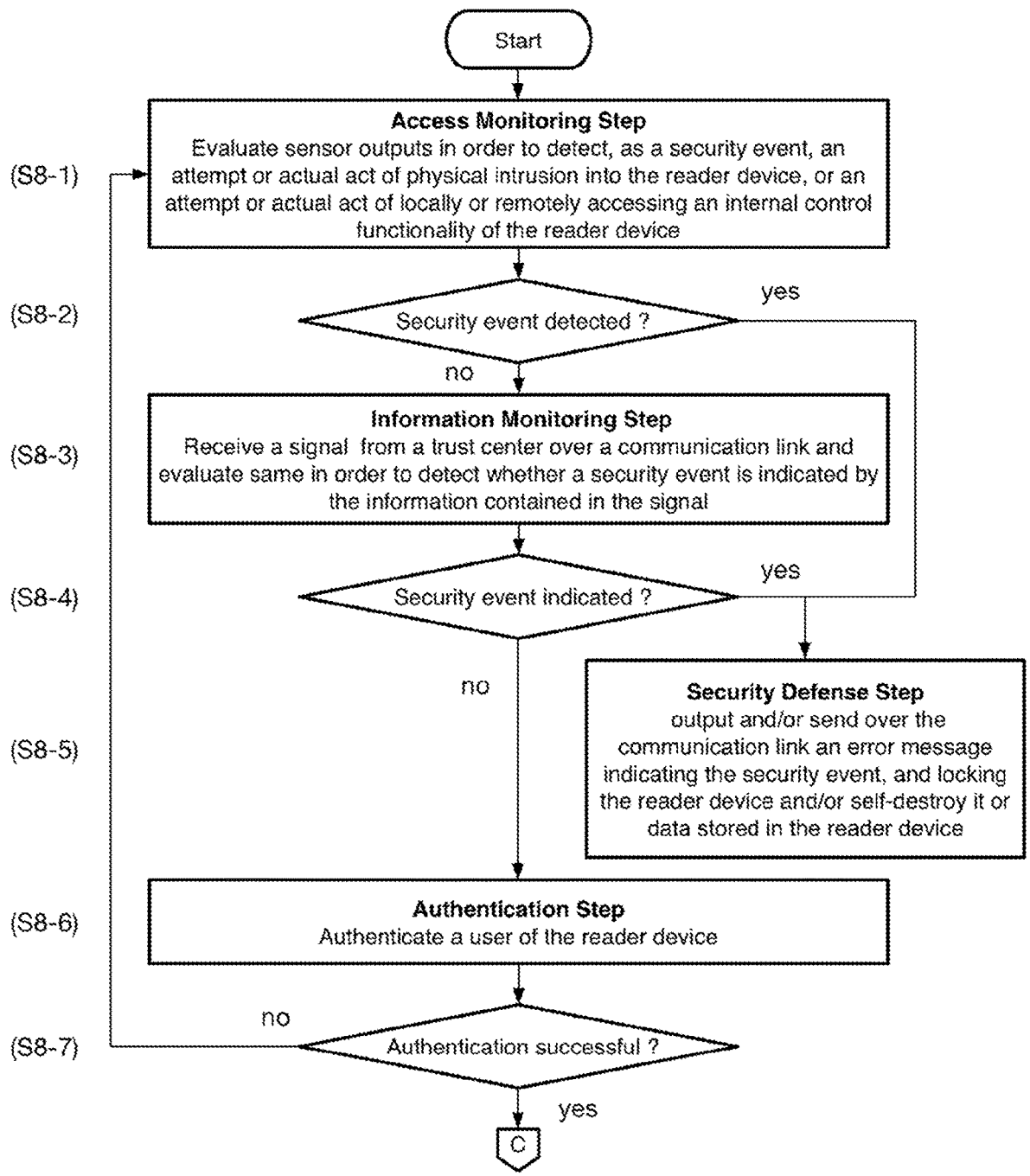
FIGS. 8A and 8B show a flow chart illustrating a method of reading with a reader device a marking, such as a composite security marking of FIG. 1, according to another preferred embodiment of the present security solution, which does not require reading a PUF as part of the reading process.
Figure 8B:
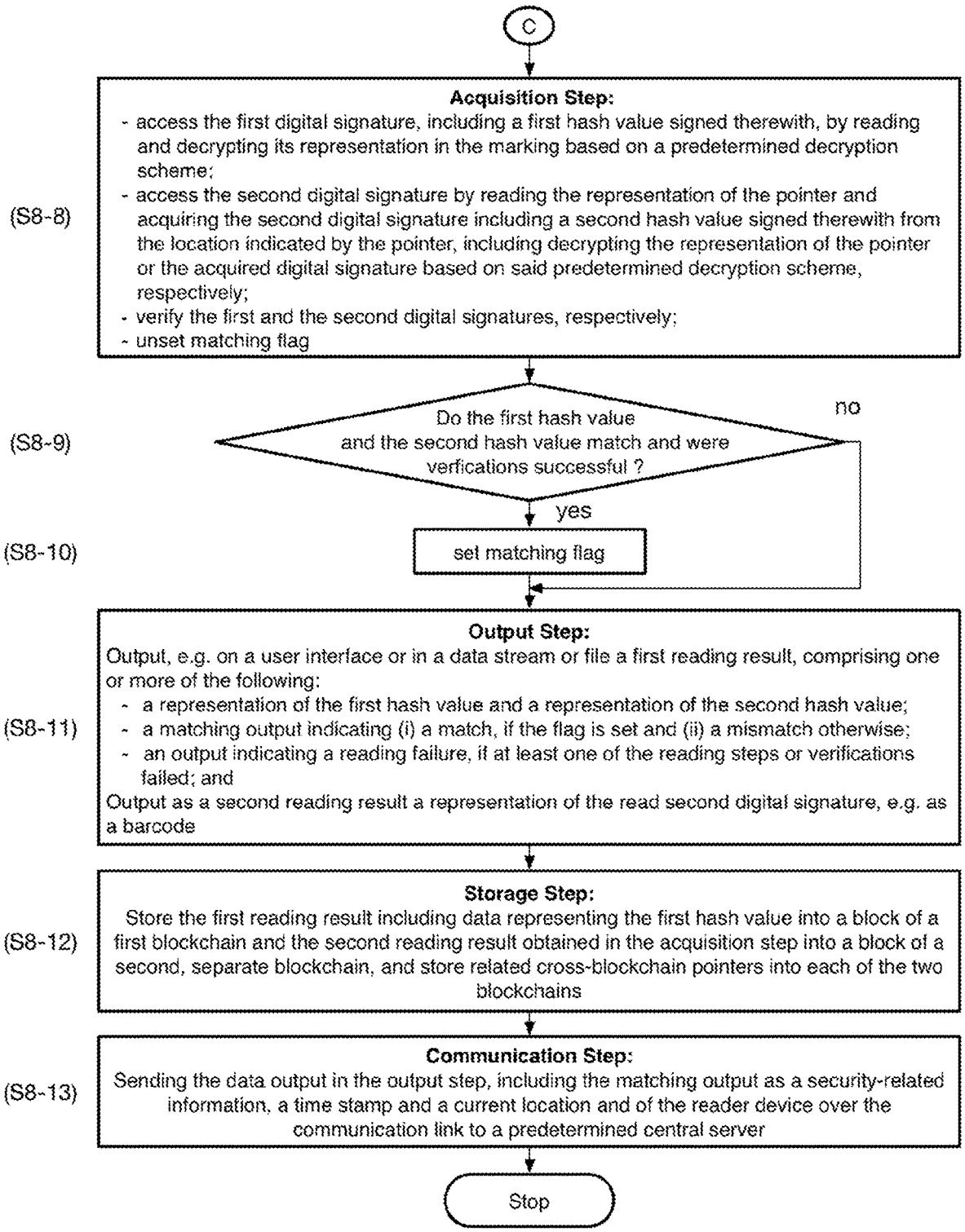

FIGS. 8A and 8B together show a flow chart (split in two parts connected via connector "C") illustrating an embodiment of yet another method of reading a marking, such as a composite security marking of FIG. 1, with a reader device. Here, the marking needs to comprise both an encrypted representation of a first digital signature and a representation of a pointer indicating a location where a second digital signature can be accessed. Unlike the embodiment of FIGS. 7A and 7B or 7C, this embodiment does not require (although it does not exclude the option of) reading a PUF as part of the reading process. Optionally, this method may comprise a similar first phase comprising steps S8-1 to S8-7 (which correspond to steps S7-1 to S7-7 of FIG. 7A) for enhancing the security of a reader device itself.

The method further comprises an acquisition step S8-8, wherein the first digital signature comprised in the marking is acquired from the marking, wherein the first digital signature comprises the first hash value signed therewith. Furthermore, the second digital signature pertaining to the marking is accessed by acquiring from the marking said pointer indicating a source where the second digital signature can be accessed, e.g. from a remote server. The second digital signature is read from said source and a matching flag is initialized (unset). In addition, both digital signatures are being verified.

In a subsequent matching step S8-9, the first hash value signed by and comprised in the acquired first digital signature and the second hash value signed by and comprised in the acquired second digital signature are compared. If the two hash values match (S8-9; yes) and the verifications were successful, the matching flag is set (step S8-10), otherwise (S8-9; no) the matching flag is not set. Of course, using such a matching flag is only one of many different possible implementations of determining and communicating whether or not the two hash values match.

The method further comprises an output step S8-11, an optional storage step S8-12, and an optional Communication step S8-13. These steps may particularly be similar to the corresponding steps S7-14 to S7-16 of FIG. 7B, such that the corresponding explanations provided above in connection with the method of FIGS. 7A and 7B also apply to steps 8-11 to 8-13, respectively. Accordingly, also this method can be used to read a marking, particularly a composite security marking as disclosed herein (e.g. in FIG. 1). Again, the reading results may particularly be used for authentication purposes in the field (e.g. at various nodes along a supply chain of products being marked) and for tracking and tracing of marked products along a supply chain. Because the method of FIGS. 8A and 8B does not require reading a PUF, it is particularly suitable of being implemented by a reader device in the form of a common portable electronic communication terminal, such as a smart phone or a portable computer, e.g. tablet computer, comprising a suitable sensor, such as a camera, to read the marking.

Figure 9:
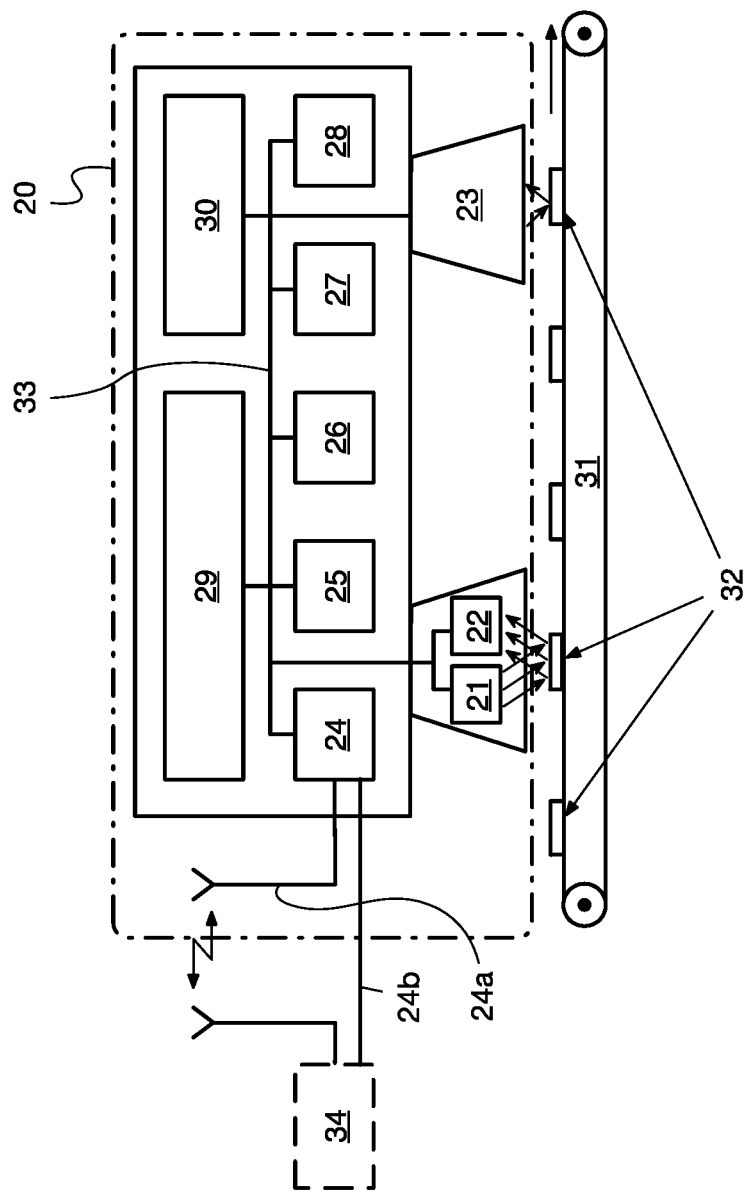
FIG. 9 schematically illustrates a reader device according to a preferred embodiment of the present security solution.

FIG. 9 schematically illustrates a reader device 20, according to a preferred embodiment of the present invention. In particular, the reader device may be adapted to perform the method of FIGS. 7A and 7B or 7C. By way of example, and without limitation, the reader device 20 may form a component of or be used in connection with a manufacturing or commission line, which is illustrated in FIG. 9 by way of a conveyor 31 on which physical objects 32, i.e. products, each bearing a composite security marking as disclosed herein (e.g. in FIG. 1) are transported to and from the reader device 20.

The reader device 20 may comprise various different components 21 to 30, which are communicatively interconnected by a data bus 33 or any other suitable communication technology. In particular, the reader device 20 comprises a stimulator 21 adapted to generate and apply to a composite security marking 1 on the product 32 passing by on the conveyor 31 a stimulation according to a predetermined challenge-response authentication scheme, and a corresponding PUF-detector 22 adapted to detect the response emitted by the PUF of the marking in reaction to the stimulation. For example, if the PUF comprises a mix of different UCDs, the stimulator 21 may be adapted to admit a suitable electromagnetic radiation in order to stimulate the UCD's in the PUF to re-emit electromagnetic radiation being characteristic for the specific PUF of the marking. Accordingly, in such case the PUF-detector is adapted to detect such a re-emitted radiation and spectrally analyze it in order to derive a digital signal, e.g. in the form of a spectral barcode, that represents the response and which can be further processed.

Furthermore, the reader device 20 may comprise an acquisition device 23 that is adapted to acquire a first digital signature comprised in the marking. In particular, the acquisition device 23 may be adapted to perform a step similar to step S7-11 of FIG. 7C.

In addition, the reader device 20 may comprise a communication device 24 that is adapted to communicate with an opposing side 34, for example a central security server of a trust center, via a communication link. Particularly, the communication link may be implemented as a wireless link, in which case the communication device would typically comprise or be connected to an antenna 24a, or the link may be implemented by way of the cable, such as electrical or optical cable, as a non-wireless communication link 24b. Particularly, the reader device 20 may be configured to send reading results to be output in the output step (as in step S7-14 of FIG. 7B, for example) over the communication link in order to inform the opposing side 34 of the reading results and/or other information, such as security-related information (e.g. the occurrence of a security event at the reader device 20).

To further increase security, the reader device 20 may also comprise an authentication device 25 being adapted to authenticate a user of the reader device 20, before permitting access to it and/or its further use (such as in steps S7-6 and S7-7 of FIG. 7A).

The reader device 20 may further comprise a security device 26 comprising one or more sensors for detecting a security event, such as an attempt or actual act of physical intrusion into the reader device 20, or an attempt or actual act of locally or remotely accessing without authorization an internal control functionality of the reader device 20. Preferably, the security device 26 interacts with or further comprises a security defense arrangement 27 to protect the reader device 20 in case a security event was detected. Particularly, the security defense arrangement 27 may be adapted to perform a step similar to step S7-5 of FIG. 7A. For example, the security defense arrangement 27 may be configured to lock a user interface of the reader device 20 in case a security event is detected or to activate a self-destruction of a security chip contained in the reader device 20, in order to protect data stored therein, including for example a private cryptographic key or other security-relevant data such as authentication data. In addition to or instead of the security device 26, the reader device 20 may comprise a monitoring device 28, that is configured to detect a security event indicated in information contained in a signal received from the opposing side 34 over said communication link. For example, in case such opposing side 34, e.g. a trust center, learns about a broader attempt to attack the security and integrity of reader devices 20 being distributed in the field, e.g. along a given supply chain, such signal may be used to proactively trigger a blocking (at least temporarily) of any further use of the reader devices 20 in the field in order to prevent tampering with the reader devices 20 by such attacks.

Furthermore, the reader device 20 comprises a processing device 29 that is particularly adapted, e.g. by a respective software program running on it, to process the digital signal generated by the PUF-detector in order to generate a hash value of the response of the PUF by application of a predetermined cryptographic hash function to the digital signal (cf. step S7-10 of FIG. 7B or 7C). In some implementations, further functionality of the reader device 20 that involves data processing or control may be additionally implemented by the processing device 29. Accordingly, all or part of any processing functionality of the other components 21 to 28 and 30 of the reader device 20 may be incorporated into the processing device 29 instead of being implemented in separate components.

The reader device may also comprise a blockchain storing device that is adapted to store data in one or more blockchains, to which the reader device 20 is connectable via said communication link. In particular, said data may correspond to the reading results generated when the reader device is used for reading a marking comprising a PUF. While the blockchain storing device may be implemented as a separate component or module of the reader device 20, it is preferably included in the processing device 29, as in FIG. 9.

An output generator 30 forms a further component of the reader device 20. It is configured to output, e.g. on a user interface or on another interface, such as an electrical or optical interface, data representing the generated hash value as a first reading result, a representation of acquired digital signatures, such as the first digital signature and the second digital signature discussed above (cf. step S7-14 of FIG. 7B) and optionally, a matching output indicating whether or not the hash values resulting from the processing step (cf. step S7-10 of FIG. 7B or 7C) and the acquisition step (cf. step S7-11 of FIG. 7C) match (cf. step S7-12 of FIG. 7C).

D. Overall Security Solution

Figure 10:
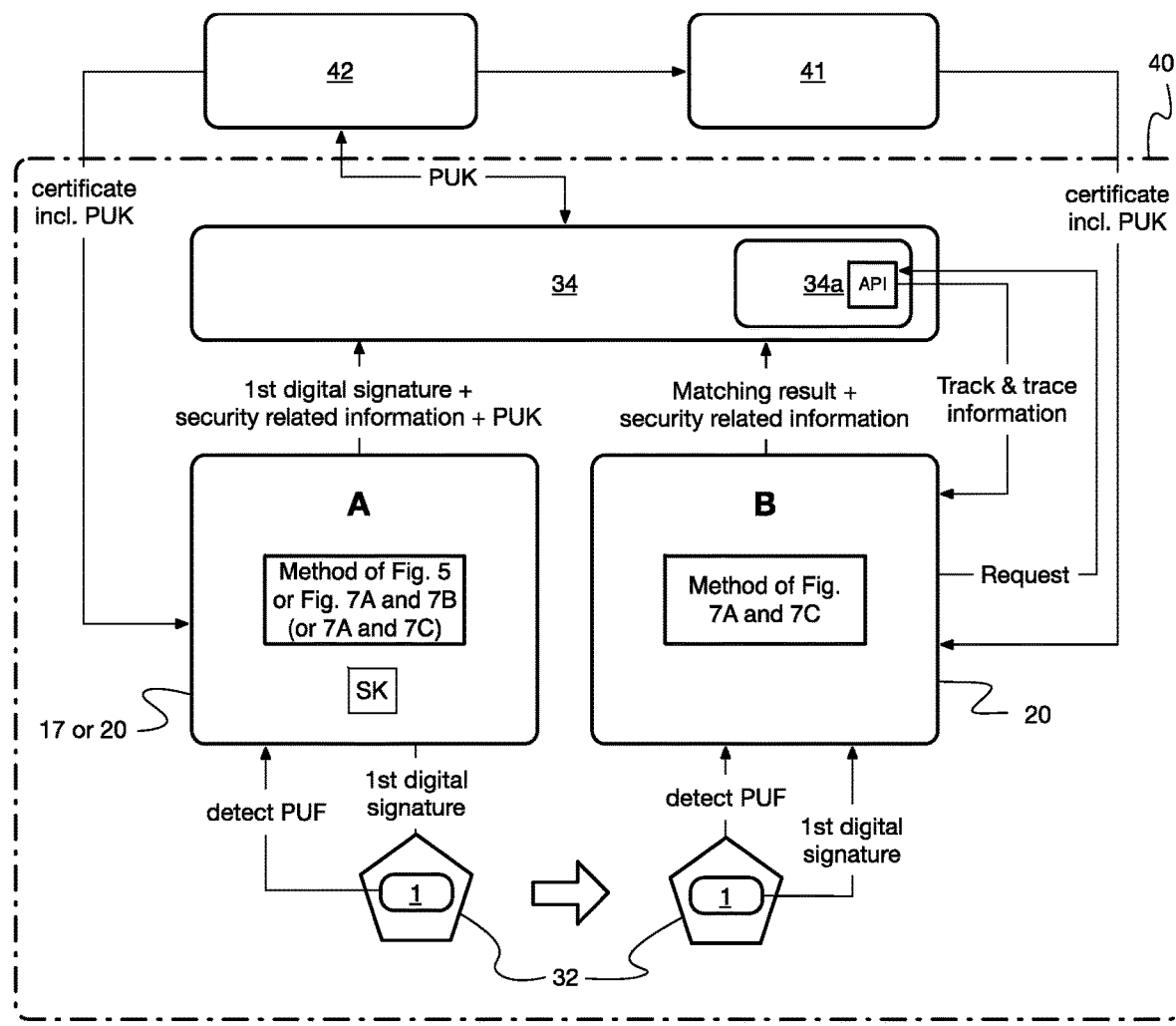
FIG. 10 is a schematic overview of a preferred embodiment of the present security solution.
Figure 11:
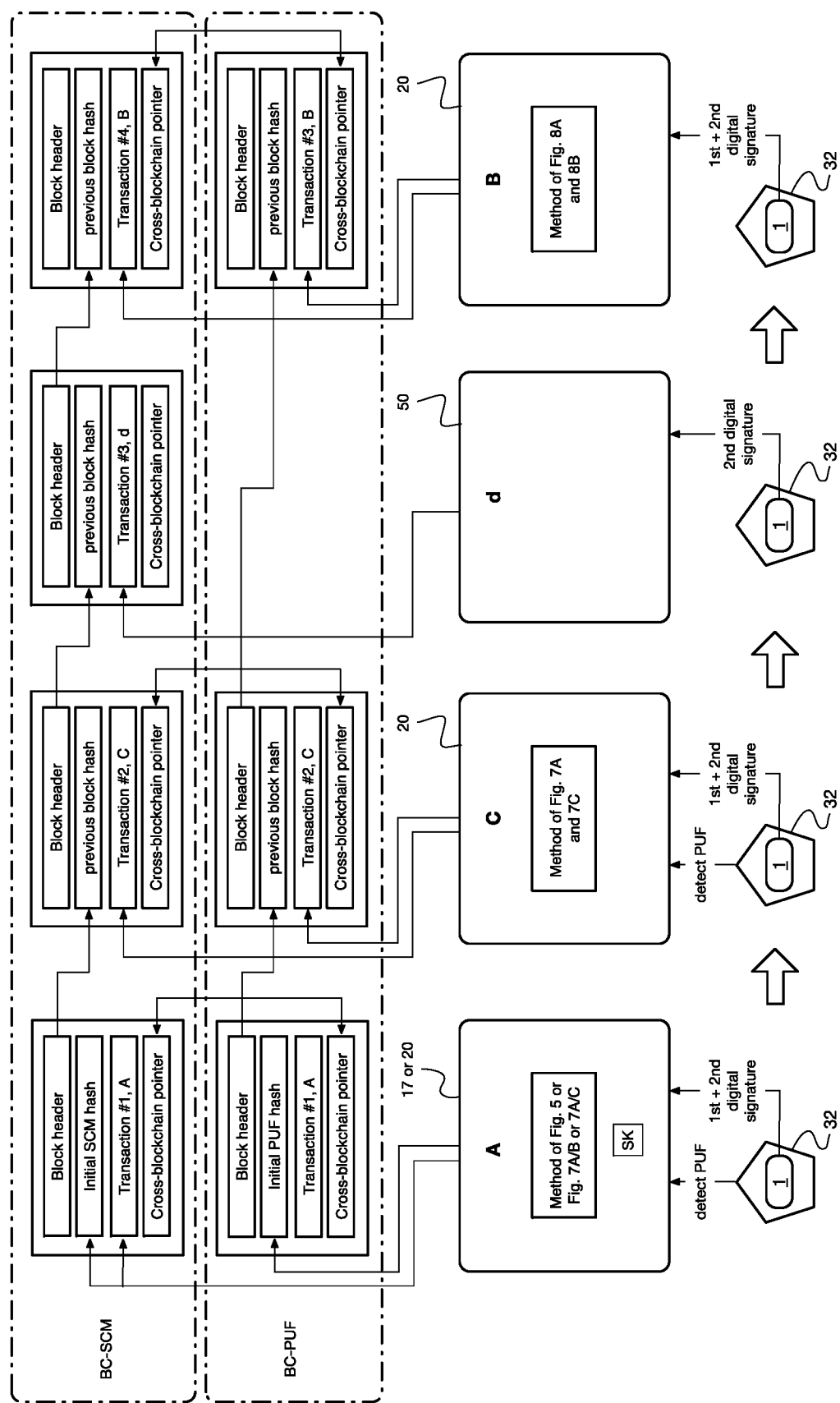
FIG. 11 schematically shows an evolution of a set of two cross-connected blockchains along a supply chain for a product being marked with a composite security marking, according to preferred embodiments of the present security solution.

FIGS. 10 and 11 illustrate further preferred aspects of the overall security solution that is based on the use of markings comprising a PUF and on one or more reader devices, as discussed above. In particular, FIG. 10 shows a schematic overview of a basic embodiment of a security system 14 based on the present security solution that allows for verifying, at a recipient B participating in a supply chain, whether a product being marked by a composite security marking 1 (e.g. per FIG. 1) is original and was in fact provided by the presumed original manufacturer A positioned upstream in the supply chain.

To that purpose, manufacturer A is equipped with an apparatus for applying a composite security marking 1 to the products 32 being subsequently shipped along the supply chain. For example, such apparatus may be an apparatus similar to the apparatus shown in FIG. 6. Alternatively, manufacturer A may be equipped with a reader device 20, such as the one shown in FIG. 9, and use a separate apparatus for applying a corresponding composite security marking 1 carrying information read by the reader device 20, including a (first) digital signature comprising a (first) hash value being derived from reading the PUF in the composite security marking 1. Accordingly, the apparatus 17 respectively 20 is configured to perform the corresponding method of FIG. 5 respectively of FIGS. 7A and 7B (and/or 7C). In addition, the apparatus 17 or 20 is equipped to generate a public/private key pair of an asymmetric cryptography system, store the private key (secure key, SK) in a secured storage space of the apparatus 17 respectively 20 and forward the public key (PUK) along with the first digital signature and optionally further security-related information, such as the time and/or location of the generation of the first digital signature, to a central security server 34 located in a trust center that is entertained by a trusted third party. Accordingly, the trust center plays the role of a registration authority, where particular public keys of one or more apparatus 17 and reader devices 20 are registered and stored. Preferably, any communication to and from the trust center is protected by encryption, in particular to prevent "man-in-the-middle attacks".

In order to increase the available security level, the public key may be provided to a certification authority of a public key infrastructure (PKI), particularly to a related certification authority server 42, where the public key is certified and included into a cryptographic certificate that is made available to manufacturer A and a validation authority (server) 41. Now, any further node in the supply chain being equipped with a reader device 20 as described herein, such as recipient B, can request the certificate from the validation authority 41 to use it for examining the marked product allegedly originating from manufacturer A for its authenticity. To that purpose, the reader device 20 at recipient B runs the method of FIGS. 7A and 7B (or 7C) and thereby detects the PUF on the composite security marking 1 of the product 32 and reads the first digital signature contained therein including the (second) hash value that is to be compared to the (first) hash value derived from the detected response of the PUF. If both hash values match, this confirms that manufacturer A was in fact the originator of the product 32, otherwise that the product or its marking have been counterfeited or otherwise tampered with.

The result of this comparison, i.e. the matching result and optionally further security-related information, such as the time and location of the examination and/or the identity of a user of the reader device 20 carrying through the examination, are forwarded to and stored on the central security server 34 of the trust center. This allows for a central monitoring of the supply chain and early identification of any counterfeiting or tampering issues occurring along the supply chain. The central security server 34 may further be configured to generate or consolidate and make available via a data interface API track and trace data reflecting the processing of the product 32 along the supply chain based on the matching results and security-related information provided by any reader devices 20 being involved in the supply chain.

FIG. 11 refers to a further preferred embodiment of the present security solution, particularly of a security system 40, wherein blockchain technology is used in order to safely store and make available authentication data being generated along the supply chain. Specifically, FIG. 11 schematically illustrates an evolution of a set of two cross-connected blockchains in parallel to a supply chain for a product 32 being marked with a composite security marking 1, according to preferred embodiments of the present security solution. Particularly, the embodiments of FIG. 10 and FIG. 11 may be combined within a single solution.

The solution of FIG. 11 comprises a first blockchain BC-PUF that is configured to safely store and make available authentication information, in particular hash values derived from detecting PUFs contained in composite security markings 1 of related products 32, as described herein. In addition, a second blockchain BC-SCM is provided, which is configured to safely store and make available supply-chain information, such as serial numbers of the products 32, dates and locations of readings of the composite security markings 1 of the products 32 etc. Particularly, such supply-chain data may be stored in the second blockchain BC-SCM in the form of or in addition to related hash values being generated from such data by application of a suitable hash function. The two blockchains BC-PUF and BC-SCM, which are both configured to track the motion of the products 32 along the supply chain, have their related blocks, i.e. the blocks containing data pertaining to the same checkpoint along the supply chain, linked by cross-blockchain pointers, thus providing references from and to corresponding blocks.

At a first node of the supply chain, which is owned by a manufacturer A of a product 32, this product 32 is marked with a composite security marking 1, as described herein, e.g. of the kind shown in FIG. 1. Again, an apparatus 17 or a reader device 20, as described above with reference to FIG. 6 respectively FIG. 9, may be used for this purpose. In the course of this marking process, the composite security marking 1 is detected by the apparatus 17 respectively 20 according to the method of FIGS. 7A and 7B (or 7C) and a respective hash value is generated. Optionally, this hash value is confirmed by comparing it to a corresponding hash value provided by the first digital signature also contained in the composite security marking 1, and then it is stored in a first block of the blockchain BC-PUF as an initial PUF hash value as part of a first stored transaction #1 originated by manufacturer A.

The composite security marking 1 of the product 32 further comprises a second digital signature that includes a second hash value being derived from supply-chain related data pertaining to manufacturer A. This second hash value is read from the composite security marking 1, using apparatus 17 respectively reader device 20, and stored to a first block of the second supply chain BC-SCM as part of a first transaction #1 originated by manufacturer A, optionally along with further supply chain related data. Both of these two first blocks contain data corresponding to the initial step of the supply chain being owned by manufacturer A and accordingly in each of the two blocks a cross-blockchain pointer to the respective corresponding block in the other blockchain is added, in order to allow for cross-referencing.

In a next step along the supply chain, product 32 reaches a second, intermediate node C, which might for example be owned by logistics company being responsible for the further transportation of the product along the supply chain. Node C is equipped with a further reader device 20 and thus performs an examination of the product 32 by running the method of FIGS. 7A and 7C on said reader device 20 in relation to the composite security marking 1 of product 32. If this examination confirms manufacturer A as the originator of the product 32, a respective transaction #2 confirming the positive examination is stored into a second block of the first blockchain BC-PUF. Otherwise, said stored transaction #2 indicates a negative result of the examination, thus indicating a fraud in relation to product 32 respectively its composite security marking 1. In addition, an alarm or error message may be output by the output generator 30, e.g. on a user interface, of the reader device 20, or an alarm/error message might be sent to the central trust center 34 via communication link 24a or 24b in order to indicate said negative result.

The second block is cross-linked to the previous, i.e. first, block of said blockchain by addition of the block hash of said previous block. This entry into the first blockchain BC-PUF confirms that the product 32 was examined at node C with the respective result. The initial PUF hash value remains available via the cross-link to the first block. Similarly, as in the previous node, supply chain information is generated from the second digital signature of the composite security marking 1 and further data related to the node and stored in the second blockchain BC-SCM as a transaction #2. Also in this second supply chain BC-SCM, the second block is cross-linked to the previous first block by storing a block hash of said previous block in the second block. Again, a cross-blockchain pointer is added in each of the second blocks to allow for cross-referencing between them.

In a next step along the supply chain, product 32 reaches a third, intermediate node d, which might for example be a remote logistic station that is not equipped with a reader device 20 but instead only with a conventional scanner that is only capable of reading the second digital signature comprised in the composite security marking 1 of product 32. Unlike in the previous nodes, at node d only supply chain related data is written to a third block of the second blockchain BC-SCM as a transaction #3, similarly as in node C. However, no data is stored in the first supply chain BC-PUF, as the scanner is not capable of reading the PUF of the composite security marking 1 and generate related data.

Finally, in a fourth step along the supply chain, product 32 reaches node B, which might for example be a final destination or a local retailer of the product 32. At this node B, a similar procedure is performed using another reader device 20, as at previous node C and accordingly, similar entries are added to respective further blocks of both blockchains BC-PUF and BC-SCM. Particularly, at such a node B or (a node C), also a reader apparatus being adapted to perform the method of the sixth aspect of the present solution, e.g. according to FIGS. 8A and 8B, may be used. Of course, instead, the method of FIGS. 7A and 7C may be applied at node B. The method of FIGS. 8A and 8B may instead also be used at a node d, as described above, in order to increase the level of examination there. This has the advantage that not only the second digital signature may be read and respective data written to the second block chain, but in addition a security examination may be performed as well. Optionally, this may comprise writing transaction data for node B to the first blockchain in a similar manner as at node C.

The two blockchains serve as a safe public ledger of all of said transactions which have ever occurred and have been stored since the initiation of said blockchains. Furthermore, the blockchains provide an extremely high integrity level as they cannot be manipulated (in practice) and thus their use further enhances the security of the overall security solution presented herein. In particular, the data stored in the two block chains can be used to examine both whether manufacturer A was in fact the originator of product 32 and whether the supply chain was as expected. This examination can be made at each node A, C, B along the supply chain that is equipped with a reader device 20 and thus can examine the composite security marking 1 of the product 32 and access the data stored in the two blockchains.

While above at least one exemplary embodiment of the present security solution has been described, it has to be noted that a great number of variation thereto exists. Furthermore, it is appreciated that the described exemplary embodiments only illustrate non-limiting examples of how the present security solution can be implemented and that it is not intended to limit the scope, the application or the configuration of the herein-described apparatuses and methods. Rather, the preceding description will provide the person skilled in the art with constructions for implementing at least one exemplary embodiment of the solution, wherein it has to be understood that various changes of functionality and the device of the elements of the exemplary embodiment can be made, without deviating from the subject-matter defined by the appended claims and their legal equivalents.

LIST OF REFERENCE SIGNS

1 Composite security marking
2 Physical unclonable function, PUF
3 Digital signature corresponding to PUF
4 Pointer indicating where digital signature can be accessed
5 Bottle containing consumable good
6 Consumable good, in particular liquid pharmaceutical substance
7 Packaging
8 Pharmaceutical tablet, pill
9 Blister pack
10 Supply of mix of different UCDs
11 Container with raw material for 3-D printing
12 Additive manufacturing device, 3-D printer
13 3-D printed physical object/product
14 PUF-Scanner
15 Processing device
16 Barcode printer
17 Apparatus for providing a composite security marking to an object
20 Reader device
21 Stimulator
22 PUF-Detector
23 Acquisition device
24 Communication device
24a Antenna
24b non-wireless communication link
25 Authentication device
26 Security device
27 Security defense arrangement
28 Monitoring device
29 Processing device
30 Output generator
31 Conveyor of a production line
32 Marked physical objects (products)
33 Bus
34 Central security server, trust center
40 Security system
41 Validation Authority server
42 Certification Authority server
C Challenge according to challenge-response authentication scheme
R Response according to challenge-response authentication scheme
F Data(string) representing response by PUF to challenge
H(F) Cryptographic hash function applied to F, yielding hash value H=H(F)
S[H(F)] Digital signature of hash value H
$\lambda$, Wavelengths
$\lambda_i$ Wavelength, at which a peak of the light intensity I occurs in the response R
I Light intensity
$I_i$ Light intensity at wavelength $\lambda_i$

The invention claimed is:

1. A composite security marking for a physical object, comprising:
    a physical unclonable function (PUF) implemented as a structure configured to generate a virtual pattern in response to a challenge; and
    an encrypted representation of a pointer indicating a location to a local or remote database or to a server address or Internet address where a digital signature can be accessed, wherein at least one of said representation of the pointer and said digital signature being accessible at the location is encrypted, such that in order to read said digital signature, the respective representation first needs to be decrypted, before said digital signature can be read;
    wherein the digital signature digitally signs a hash value resulting from application of a predetermined cryptographic hash function to data representing a response generated by the PUF in reaction to a challenge of a predetermined challenge-response authentication scheme, wherein said data representing the response generated by the PUF in reaction to a challenge of a predetermined challenge-response authentication scheme for said structure configured to generate the virtual pattern represents at least one recognized aspect or portion of said virtual pattern.

2. The composite security marking according to claim 1, wherein the composite security marking comprises said pointer and said pointer indicates a routing to a data source that is accessible through a communication link and from which the digital signature is retrievable.

3. A physical object, comprising a composite security marking according to claim 1.

4. A method of reading, with a reader device, a composite security marking according to claim 1, the method comprising the following steps:
- a stimulation step, wherein a physical challenge according to a predetermined challenge-response authentication scheme corresponding to the PUF is created and applied to a PUF;
- a detection step, wherein a response generated by the PUF in accordance with the challenge-response authentication scheme in reaction to the challenge is detected and a digital signal representing the response is generated;
- a processing step, wherein the digital signal is processed in order to generate a first hash value of the response by application of a predetermined cryptographic hash function to the digital signal;
- an acquisition step, comprising accessing said first digital signature to recover from it a second hash value signed therewith, by:
  - reading and decrypting the representation of the first digital signature in the marking based on a predetermined decryption scheme, or
  - reading the representation of the pointer in the marking and acquiring and verifying the first digital signature from the location indicated by the pointer, including decrypting the representation of the pointer or the first digital signature according to the decryption scheme, respectively; and
- an output step, comprising outputting a first reading result comprising at least one of:
  - a representation of the first hash value and a representation of the second hash value,
  - a matching output indicating whether, according to at least one predetermined matching criterion, the first hash value matches said second hash value, or
  - an output indicating a reading failure.

5. The method of claim 4, wherein in the processing step the digital signal is generated in such a way that it represents at least one PUF-specific distinctive property of the response that is, at least substantially, invariant under variations of the environmental conditions at which the response is detected.

6. The method of claim 4, wherein the output step comprises digitally signing data containing the generated first hash value and outputting the resulting digital signature as part of the reading result.

7. A method of reading with a reader device a marking, particularly a composite security marking according to claim 1, that comprises both an encrypted representation of a first digital signature and a representation of a pointer indicating a location where a second digital signature can be accessed, the method comprising:
- an acquisition step comprising:
  - accessing the first digital signature, including a first hash value signed therewith, by reading and decrypting its representation in the marking based on a predetermined decryption scheme and by verifying it; and
  - accessing the second digital signature by reading the representation of the pointer and acquiring the second digital signature including a second hash value signed therewith from the location indicated by the pointer, including decrypting the representation of the pointer or the acquired encrypted second digital signature based on said predetermined decryption scheme, respectively, and verifying the second digital signature;
- an output step comprising outputting a first reading result comprising one or more of the following:
  - a representation of the first hash value and a representation of the second hash value;
  - matching output indicating whether, according to at least one predetermined matching criterion, the first hash value matches the second hash value; and
  - an output indicating a reading failure.

8. The method of claim 7, wherein the acquisition step further comprises:
- acquiring from the marking a further digital signature or a pointer indicating a source where a particular further digital signature pertaining to the marking can be accessed; and
- the output step further comprises outputting a representation of the acquired further digital signature as a second reading result.

9. The method of claim 7, further comprising a storage step, wherein the first reading result is stored into a block of a first blockchain or into one or more node of a first blockless distributed ledger.

10. The method of claim 9, wherein:
- the storage step further comprises storing the second reading result into a block of second blockchain being separate from the first blockchain or into one or more nodes of a second blockless distributed ledger being separate from the first blockless distributed ledger, respectively; and
- storing the first reading result comprises storing data representing the first hash value into a block of the first blockchain or into one or more nodes of the first blockless distributed ledger, respectively.

11. The method of claim 10 wherein:
if the storage step relates to blockchains:
- storing the data representing the first hash value into a block of the first blockchain further comprises storing a cross-blockchain pointer, which logically maps said block of the first blockchain to a corresponding block of the second blockchain, into said block of the first blockchain; and
- storing the data representing the second hash value in a block of the second blockchain further comprises storing a cross-blockchain pointer, which logically maps said block of the second blockchain to a corresponding block of the first blockchain, into the block of the second blockchain; and if the storage step relates to blockless distributed ledgers:
- storing said at least one of said hash values into a node of the first blockless distributed ledger comprises storing a cross-ledger pointer, which logically maps the node of the first blockless distributed ledger to a corresponding node of the second blockless distributed ledger, into the node of the first blockless distributed ledger; and
- storing the supplementary information into a node of the second blockless distributed ledger comprises storing a cross-ledger pointer, which logically maps the node of the second blockless distributed ledger to a corresponding node of the first blockless distributed ledger, into the node of the second blockless distributed ledger.

12. A reader device for reading a marking, wherein the reader device is adapted to perform the method of claim 4.

13. A non-transitory computer-readable medium including a computer program comprising instructions, which when executed on one or more processors of a reader device causes the reader device to perform method of claim 4.

14. The composite security marking according to claim 1, wherein the virtual pattern is an optical interference pattern.

15. The composite security marking according to claim 14, wherein the structure configured to generate the virtual pattern comprises a microstructure including a plurality of semiconductor particles having optical and electronic properties that are different from optical and electronic properties of larger semiconductor particles, wherein the plurality of semiconductor particles are configured to emit light of specific wavelengths in response to the challenge.

16. The composite security marking according to claim 1, wherein the composite security marking is an anti-counterfeit product marking.

17. A method of providing a physical object, the method comprising:
- adding a physical unclonable function (PUF) to an object to be marked, wherein the PUF comprises a structure configured to generate a virtual pattern in response to a challenge;
- applying a challenge of a predetermined challenge-response authentication scheme to said PUF to trigger a response according to said authentication scheme in reaction to said challenge;
- detecting said response;
- applying a predetermined cryptographic hash function to data representing said response to obtain a hash value, wherein said data representing said response generated by the PUF in reaction to a challenge of a predetermined challenge-response authentication scheme for said structure configured to generate the virtual pattern represents at least one recognized aspect or portion of said virtual pattern;
- signing said hash value with a digital signature; and
- adding an encrypted representation of a pointer indicating a location to a local or remote database or to a server address or Internet address where the digital signature can be accessed to the object to be marked, wherein at least one of said representation of the pointer and said digital signature being accessible at the location is encrypted, such that in order to read the digital signature, the respective representation first needs to be decrypted, before the digital signature can be read.

18. The method according to claim 17, wherein the step of adding the PUF to an object to be marked comprises one or more of the following:
- adding the PUF to a coating material to obtain a PUF-enhanced coating material and applying the PUF-enhanced coating material to a physical object to be marked;
- adding a PUF to a raw material or an intermediate material before or while producing thereof a physical object to be marked; or
- adding a PUF to a raw material or fusion agent of an additive manufacturing process, for producing a physical object to be marked or at least a part of such object.

19. An apparatus for providing a physical object with a composite security marking, wherein the apparatus is adapted to perform the method of claim 17.

20. The method according to claim 17, wherein the physical object is a product with a composite security marking.

* * * * *